United States Patent
Tiernan et al.

(10) Patent No.: US 7,535,228 B2
(45) Date of Patent: May 19, 2009

(54) SENSOR ARRAY FOR NUCLEAR MAGNETIC RESONANCE IMAGING SYSTEMS AND METHOD

(75) Inventors: Timothy C. Tiernan, Newton, MA (US); John Chetley Ford, Lexington, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 415 days.

(21) Appl. No.: 11/386,449

(22) Filed: Mar. 21, 2006

(65) Prior Publication Data

US 2007/0222433 A1 Sep. 27, 2007

(51) Int. Cl.
*G01V 3/00* (2006.01)
(52) U.S. Cl. ...................... 324/318; 600/409
(58) Field of Classification Search ................. 324/318, 324/301, 248; 505/162, 845, 846; 600/409
See application file for complete search history.

(56) References Cited

U.S. PATENT DOCUMENTS

| | | | |
|---|---|---|---|
| 4,318,043 A | 3/1982 | Crooks et al. | |
| 4,607,225 A | 8/1986 | Crooks | |
| 5,155,435 A | 10/1992 | Kaufman | |
| 5,250,901 A | 10/1993 | Kaufman et al. | |
| 5,386,191 A | 1/1995 | McCarten et al. | |
| 5,699,801 A | 12/1997 | Atalar et al. | |
| 6,150,809 A | 11/2000 | Tiernan et al. | |
| 6,263,229 B1 | 7/2001 | Atalar et al. | |
| 6,477,398 B1 * | 11/2002 | Mills .......................... | 600/409 |
| 7,375,514 B2 * | 5/2006 | Rempt et al. ................ | 324/238 |
| 7,382,129 B2 * | 6/2008 | Mills .......................... | 324/318 |
| 2002/0073869 A1 | 6/2002 | Tiernan et al. | |
| 2002/0115931 A1 | 8/2002 | Strauss et al. | |
| 2003/0029345 A1 | 2/2003 | Tiernan et al. | |
| 2004/0147833 A1 * | 7/2004 | Czipott et al. .............. | 600/410 |
| 2004/0147834 A1 * | 7/2004 | Czipott et al. .............. | 600/410 |
| 2004/0169509 A1 * | 9/2004 | Czipott et al. .............. | 324/246 |
| 2004/0244625 A1 | 12/2004 | Tiernan et al. | |

(Continued)

OTHER PUBLICATIONS

Correia, et al., "Intravascular magnetic resonance imaging of aortic atherosclerotic plaque composition," Arterioscler Thromb Vasc Biol., 17, pp. 3626 (1997).

(Continued)

*Primary Examiner*—Brij Shrivastav
*Assistant Examiner*—Megann E Vaughn
(74) *Attorney, Agent, or Firm*—Townsend and Townsend and Crew LLP

(57) ABSTRACT

The present invention generally provides improved devices, systems, and methods for measuring materials with NMR and/or MRI. Exemplary embodiments provide a sensor array for NMR mapping of the material. For example tissue can be measured with the sensor array mounted on a probe body having a distal portion which can be inserted through a minimally invasive aperture. While many tissues can be measured and/or diagnosed, one exemplary embodiment includes a probe adapted for insertion into a lumen of a blood vessel. The sensor array can provide improved spatial resolution of tissue and/or tissue structures positioned near the sensor array to diagnose potentially life threatening diseases, for example a fibrous cap covering a vulnerable plaque. In specific embodiments, the sensors are attached to an expandable member, for example a balloon, which can be inflated to urge the probe sensors radially outward to position the sensors near the tissue structures.

21 Claims, 15 Drawing Sheets

U.S. PATENT DOCUMENTS

2005/0054914 A1    3/2005    Duerk et al.
2005/0116713 A1*   6/2005    Barbic ..................... 324/318
2007/0161888 A1*   7/2007    Sherman et al. ............ 600/409

OTHER PUBLICATIONS

Hargreaves, B., "Bloch Equation Simulator," Downloaded from world-wide web: http://www-mrsrl.stanford.edu/~brian/mritools.html (2005).

Lorrain, P., et al., "Electromagnetic fields and waves," 2nd Edition, WH Freeman, San Francisco, p. 387 (1970).

Perlo, et al., "High-resolution NMR sepctroscopy with a portable single-sided sensor," Science v.308, p. 1279 (May 27, 2005).

Rogers, et al., "Characterization of Signal Properties in Atherosclerotic Plaque Components by Intravascular MRI," Arterioscler Thromb Vasc Biol., 23, pp. 346- (2003).

Rourke, et al., "The Inverse Scattering Transform and Its Use in the Exact Inversion of the Bloch Equation for Noninteracting Spins," J. Magn. Reson. 99, pp. 118-138 (1992).

Worthley, et al., "A novel nonobstructive intravascular MRI coil: in vivo imaging of experimental atherosclerosis," Arterioscler Thromb Vasc Biol 23, pp. 346-350 (Feb. 2003).

* cited by examiner

SENSOR ARRAY FOR NUCLEAR MAGNETIC RESONANCE IMAGING SYSTEMS AND METHOD

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

BACKGROUND OF THE INVENTION

The present invention generally relates to the measurement of tissue and other materials, often so as to diagnose vulnerable plaque, colon cancer, and other diseases of tissues adjacent body lumens or the skin. Embodiments of the invention may employ insertable probes utilizing magnetic resonance imaging (MRI) and/or nuclear magnetic resonance (NMR) phenomena.

Many diseases exist that can be successfully treated if diagnosed in a timely manner. Examples of such life threatening diseases that can be successfully treated include atherosclerosis and cancer. A variety of diagnostic imaging modalities have been developed to help diagnose these and other diseases including ultrasound, angiography, optical coherence tomography (OCT), thermography, spectroscopy, and MRI. Unfortunately, current techniques and apparatus used to diagnose diseases are often less than ideal, in some instances being ineffective and/or too complex or costly to implement on a routine clinical basis. Failures and delays in diagnosing life threatening diseases such as cancer and atherosclerosis can lead to morbidity and/or mortality.

Atherosclerosis, a hardening and/or thickening of the arteries, is a leading cause of mortality and morbidity in the United States. Atherosclerosis is a progressive pathological process, often involving the slow buildup of fatty substances, cholesterol, cellular waste products, calcium, and fibrin in the arterial wall that can lead to blockage of the artery, and that can be a factor in multiple conditions including coronary heart disease, myocardial infarction, angina pectoris, cerebral vascular disease, thrombotic stroke, transient ischemic attacks, organ damage, vascular complications of diabetes, and/or the like.

Interventional treatments of standard plaques include coronary artery bypass surgery, percutaneous transluminal angioplasty, and stenting, with these therapies generally being targeted at hemodynamically significant stenoses identified by conventional x-ray angiography. These treatments are often quite effective in treating standard calcified and other stenotic plaques, and drug-eluting stents may extend the benefits within the coronary arteries. However, the materials and potential effects of plaques may vary between different patients, and even between different lesions of a single patient. Some plaques, and particularly those referred to as "vulnerable plaque" (which may be characterized by one or more particular materials or structural forms) may play a disproportionate role in acute coronary syndromes and sudden heart attacks.

The components of vulnerable plaques may include a soft or even liquid lipid-rich substance and a hard, collagen-rich tissue cap. In postmortem studies, vulnerable plaques may be characterized by a thin (in some cases less than 65 microns) fibrous cap, a large lipid-rich pool, and increased macrophage activity. Treatments appropriate for standard stenotic plaques may be undesirable for such lesions, as a disruption of the fibrous cap integrity in these rupture-prone plaques may release procoagulant factors, resulting in thrombus formation and the potential for an acute coronary event. Therefore, practical diagnostic techniques able to distinguish vulnerable, high-risk, rupture-prone plaque from low-risk, calcified plaques could prove very valuable in evaluation and treatment of atherosclerosis-related cardiovascular disease. As known techniques for characterizing plaques have not yet gained wide acceptance, a need exists for new and improved techniques to identify and diagnose patients with vulnerable plaque.

Colon cancer is also a major cause of death, and can affect the population at a relatively early age. Colon cancer can be successfully treated, and both diagnosis and treatment are available. Nevertheless, for a number of reasons, colon cancer continues to take lives. In some cases, this may be related to inadequacy of known colonoscopy techniques in identifying cancerous lesions. While cancerous polyps may be anatomically distinct, some cancers can manifest themselves as a thickening of the colon wall, which can be difficult to evaluate. Therefore a need exists for an improved probe that can be used in conjunction with colonoscopy to resolve these ambiguous cases, potentially resulting in improved diagnostic efficacy.

There are still other clinical applications where there exists a need to examine suspicious areas identified during examination with visible light. These include broncoscopy, urethral, esophageal and skin examinations, and the like.

While MRI has shown promise for the diagnosis of diseases, current NMR systems and images have limitations that have limited the application of these techniques. In particular, standard NMR images of small and/or internal tissue structures may have a resolution which is less than ideal for detecting and diagnosing fine tissue structures implicated with many diseases, including the fibrous cap of atherosclerotic plaque and the thicker colon walls that can be associated with colon cancer. Also, current MRI systems can be costly and bulky, and a patient scan can take several minutes.

While known MRI systems have allowed a large number of patients to benefit from diagnostic imaging, still further improvements would be desirable. For example, it would be advantageous to provide smaller MRI systems that are compatible with existing diagnostic equipment. Decreased patient scan time would also be desirable and help to integrate MRI with current diagnostic tests. It would also be advantageous to more effectively diagnose diseases, for example with high resolution MRI images. At least some of these potential advantages may be realized by the systems, devices, and methods described herein below.

BRIEF SUMMARY OF THE INVENTION

The present invention generally provides improved devices, systems, and methods for measuring tissues and other materials with MRI. Exemplary embodiments provide a sensor array for NMR mapping and imaging of the material. Tissue can be measured with the sensor array mounted on a probe body having a distal portion that can be inserted through a minimally invasive aperture or body orifice. While many tissues can be measured and/or diagnosed, one exemplary embodiment includes a probe adapted for insertion into a lumen of a blood vessel. The sensor array can provide improved spatial resolution of tissue and/or tissue structures positioned near the sensor array to diagnose potentially life threatening diseases, including a fibrous cap covering a vulnerable plaque. In specific embodiments, the sensors are attached to an expandable member, for example a balloon that can be inflated to urge the probe sensors radially outward near the tissue structures of interest.

In a first aspect, the invention provides a device for NMR mapping of a material. The invention includes a magnet to orient nuclei of the material, and a coil to excite the oriented nuclei and induce an emission of NMR signals. An array of magnetoresistive sensors detects at least one of a magnetic field amplitude or a magnetic field phase of the NMR signals, and each sensor occupies an array site to map detected signal locations.

In exemplary embodiments, the magnetoresistive sensors are selected and arranged to provide improved sensitivity of NMR measurements. For example, the magnetoresistive sensors can be arranged to detect the NMR signals in quadrature. In specific embodiments, each sensor is sensitive to a magnetic field along a single direction in a sensor plane, and the axes of the sensors are arranged to detect the NMR signals in quadrature. The magnetoresistive sensors can include at least one of an anisotropic magnetoresistive sensor, a tunneling magnetoresistive sensor or a colossal magnetoresistive sensor. In some embodiments the magnetoresistive sensors may include at least one giant magnetoresistive sensor.

In exemplary embodiments the sensors, magnet and coil are arranged to provide a compact device. For example, the magnet can be positioned in proximity to the sensor array. Also, several magnets can be used to orient the nuclei of the material and each of the magnets can be positioned in proximity to at least one sensor. The magnet can comprise at least one of an electromagnet or a permanent magnet, and the radiofrequency coil can be positioned in proximity to the sensor array. An external induction coil can power the radiofrequency coil with inductive coupling, or a conductor can conductively couple the radiofrequency coil to a power source. The magnet can be positioned in proximity to the coil and the sensor array.

Many embodiments include a display to show an NMR image of the material to a user, and a processor to map the signals from the sensors to the image. The material can include tissue of a patient, and the processor can superimpose the image on an anatomic image of the patient. The image can include at least one of a radiographic projection image, a CT image, an MRI image, or an ultrasound image.

Exemplary embodiments include NMR signals to characterize the material. For example, the NMR signals can include at least one of a free induction decay signal, a spin echo signal or a sequence of spin echo signals. The NMR signals can include encoding to determine a slice for the locations of the signals in the material. The magnet can generate a static inhomogeneous magnetic field and the signal encoding can include at least one of a radiofrequency excitation phase encoding, a radiofrequency excitation frequency encoding, or a radiofrequency excitation amplitude encoding in the static inhomogeneous magnetic field. The NMR signal can correlate with at least one of a nuclear density, a spin lattice relaxation time, a transverse relaxation time, a diffusion, a magnetization transfer, a flow or a spectral distribution within the material. At least one contrast agent can be used to enhance the NMR signals.

Specific embodiments of the device include beneficial structures. For example, a protective enclosure can be used to protect at least one of the sensors, the coil or the magnet. A structure having a cavity formed therein, for example a bore in a magnet, can be provided to position the material in the cavity near the sensors.

In another aspect, the invention provides a probe for measuring a tissue. The probe includes a body and an array of sensors. The body has a proximal portion and a distal portion that is insertable into a minimally invasive aperture. The array of sensors are sensitive to at least one of a magnetic field amplitude or a magnetic field phase, and each sensor occupies an array site to map an NMR signal from an associated measurement region of the tissue.

In specific embodiments the sensors are arranged in rows. The distal portion of the body can have an axis extending toward a distal end of the body, and the rows can extend axially along the probe. Each sensor can have a field of view and each row can have an angular orientation arranged to separate the field of view of each sensor in a first row from the field of view of each sensor in a second row.

In many embodiments, the distal portion of the body has an axis extending toward a distal end of the body, and the probe is adapted to fit within a tissue structure as the probe is advanced along the axis. The sensors can be positioned circumferentially around the axis.

In specific embodiments, the probe body is flexible, which can be beneficial for tissue measurements. For example, the probe body can include a flexible substrate, for example polyimide, having a printed circuit etched thereon, and the circuit can be connected with the sensors. The distal portion of the probe body can be adapted to deform to place the sensors in proximity with a tissue structure. For example, the probe body can include an expandable balloon to deform the distal portion of the probe body and place the sensors in proximity with the tissue structure. The probe body can be adapted for insertion into a vaginal, rectal, bronchial, urethral or esophageal body cavity. For example, the distal portion of the probe body can be disposed on a distal end of a catheter, and the probe adapted to measure a blood vessel. The tissue can include skin tissue and the probe can be adapted to lie on a surface of the skin tissue. The distal portion of the body can comprises a tube to drain fluid from the tissue, for example where the probe is implanted in tissue.

In another aspect the invention provides a method of forming an NMR image of a material. Nuclei of the material are oriented with a magnet and excited with a coil to induce an emission of NMR signals. At least one of a magnetic field amplitude or a magnetic field phase of the NMR signals are measured from the material with a plurality of magnetoresistive sensors, and each sensor occupies an array site on a probe. The signal from each sensor is mapped to a location in the image substantially dependent on the site on the probe.

In many embodiments, the NMR signals are spatially encoded to provide a depth of the signal from each sensor. The signal measured with each sensor can be mapped to the location in the image in correlation with the signal depth and sensor position on the probe.

In exemplary embodiments, the material includes a tissue with a structure, and the array is conformed to the tissue structure to position the sensors near the tissue structure. For example, an expandable member can be inflated to radially urge the sensors toward the tissue structure such as a vessel wall.

In another aspect, the invention provides a flexible NMR assembly including a magnet, a coil and a magnetic field sensor. The magnet generates a magnetic field along an axis to generate an orientation of nuclei along the axis. The coil excites the oriented nuclei to detect the nuclei with the sensor. The magnetic field sensor is sensitive to magnetic fields extending along a sensor plane, and the sensor plane oriented to avoid detection of the magnetic field with the sensor. At least one of the sensor, the coil or the magnet is arranged to allow the assembly to flex. The assembly can include flexible substrate which supports the magnet, the coil and the sensor.

DETAILED DESCRIPTION OF THE INVENTION

Figure 1A:
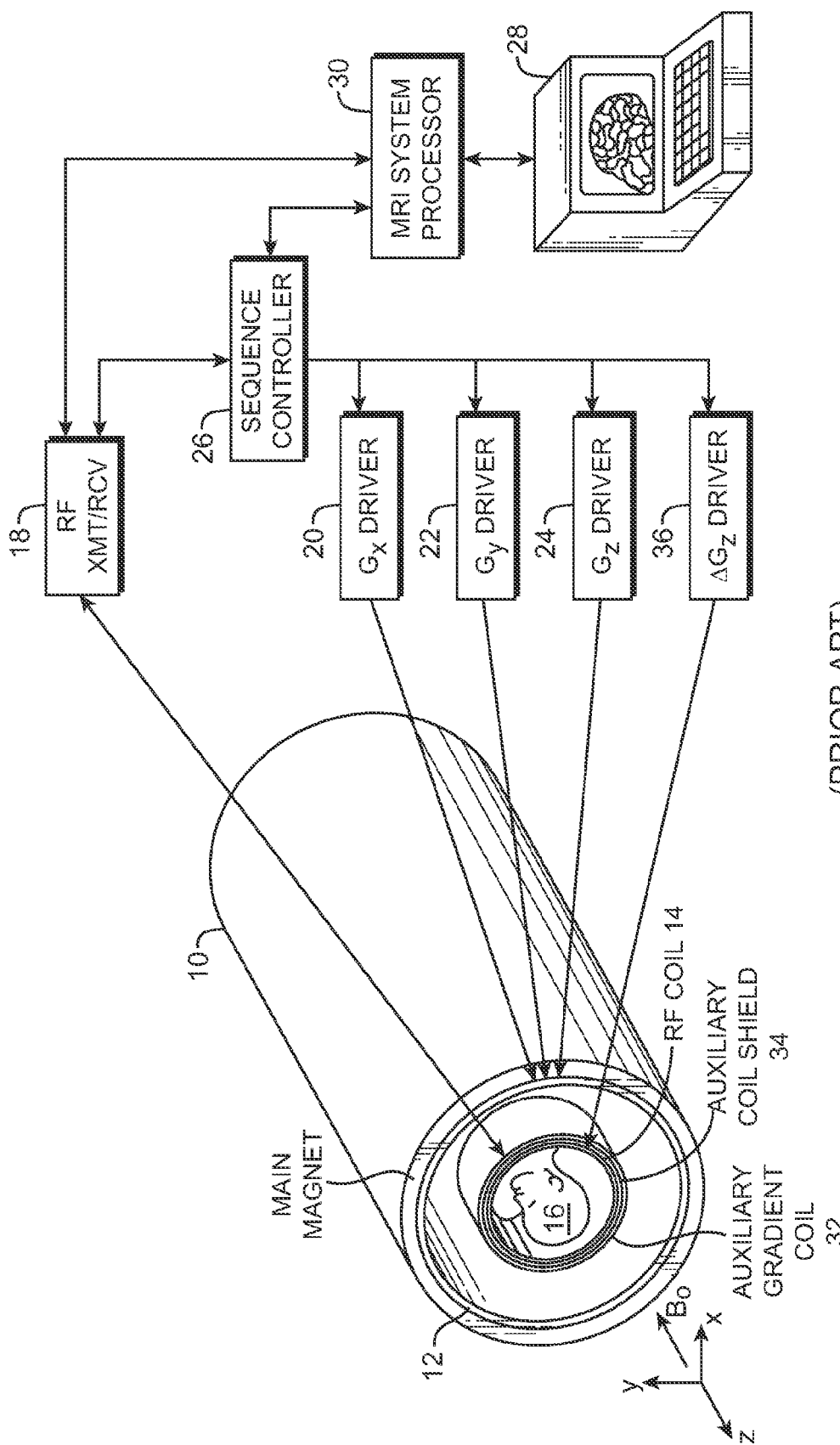
FIG. 1A schematically illustrates a prior art MRI system.

Embodiments of the present invention are directed to improved MRI systems and methods. Many of these systems incorporate sensors based on the anisotropic magnetoresistive effect or giant magnetoresistive effect (AMR and GMR, respectively). These magnetoresistive effects include, but are not limited to the anisotropic magnetoresistive effect, tunneling magnetoresistive effect, colossal magnetoresistive effect, and giant magnetoresistive effect. Many of the sensor arrays described herein permit the formation of images by direct signal localization, rather than by frequency encoding. Although embodiments will be discussed below in terms of a catheter probe to be used principally in the imaging of the coronary arteries, similar configurations can be used for examining suspicious areas of the colon identified during colonoscopy, or in broncoscopy, urography, or for examination of the skin, and other applications, for example NMR testing of ground water for contamination.

In a preferred embodiment, the sensors described herein are integrated with small magnets and RF transmit coils to provide self-contained probes. Though the sensor arrays obviate the need for gradient coils, they can also obviate the need for large RF receive coils, and some alternative embodiments may use magnetoresistive sensors in conjunction with large external magnets and/or RF transmit coils which are separated from the sensors. Because the gradient coil and power supply (gradient subsystem) can limit performance, obviating the need for these components may create a fundamentally different environment in which MRI is practiced. For instance, a major limitation on pulse sequence design can be the time associated with stabilization of the gradient magnetic field. This time can slow down imaging speed and decreases the efficiency (signal-to-noise) of the imaging process.

MRI is a well-known and commercially available non-invasive procedure for obtaining diagnostic information about the internal structures of living tissue. Elements of known MRI systems and methods can optionally be incorporated into embodiments of the systems and methods of the present invention. In very brief summary, NMR nuclei (e.g., hydrogen, sodium, phosphorous) are nominally aligned, or oriented, with a static homogeneous magnetic field $B_0$. By applying predetermined sequences of NMR RF nutation pulses and magnetic gradient pulses of selected duration and in selected directions (e.g., to selectively cause transient gradients in the $B_0$ magnetic field along the usual orthogonal x, y, z coordinate directions), some of these nuclei are disturbed, or excited, in a predetermined manner from their equilibrium orientations. As they return to the low energy orientation, they emit characteristic spatially encoded RF signals which are detected, digitized and processed in known ways to produce a visual image representing the distribution of NMR nuclei (e.g., along selected planar "slice" volumes of the living tissue) within a predetermined image volume.

In conventional commercially available MRI systems, there are different geometries and coordinate systems used to practice MRI. For example, one common arrangement uses a solenoidal cryogenic super conducting electromagnet to produce the nominally static homogeneous stable magnetic field $B_0$ along a z axis centered within the bore of the solenoid, as described in U.S. Pat. No. 4,607,225 issued to Crooks Aug. 19, 1986, entitled "Apparatus and method for reducing spurious currents in NMR imaging apparatus induced by pulsed gradient fields," the full disclosure of which is incorporated herein by reference. Another arrangement uses an array of permanent magnets and magnetic circuit yokes between enlarged pole pieces disposed above and below the image volume, as described in U.S. Pat. No. 5,386,191, to McCarten, et al. issued on Jan. 31, 1995, and entitled "RF coil providing reduced obstruction access to image volume in transverse magnet MRI system." Yet another arrangement uses a ferromagnetic core and superconducting coils to produce the $B_o$ field, as described in U.S. Pat. No. 5,250,901, issued to Kaufman, et al. on Oct. 5, 1993, and entitled "Open architecture iron core electromagnet for MRI using superconductive winding," the full disclosure of which is also incorporated herein by reference.

Figure 1B:
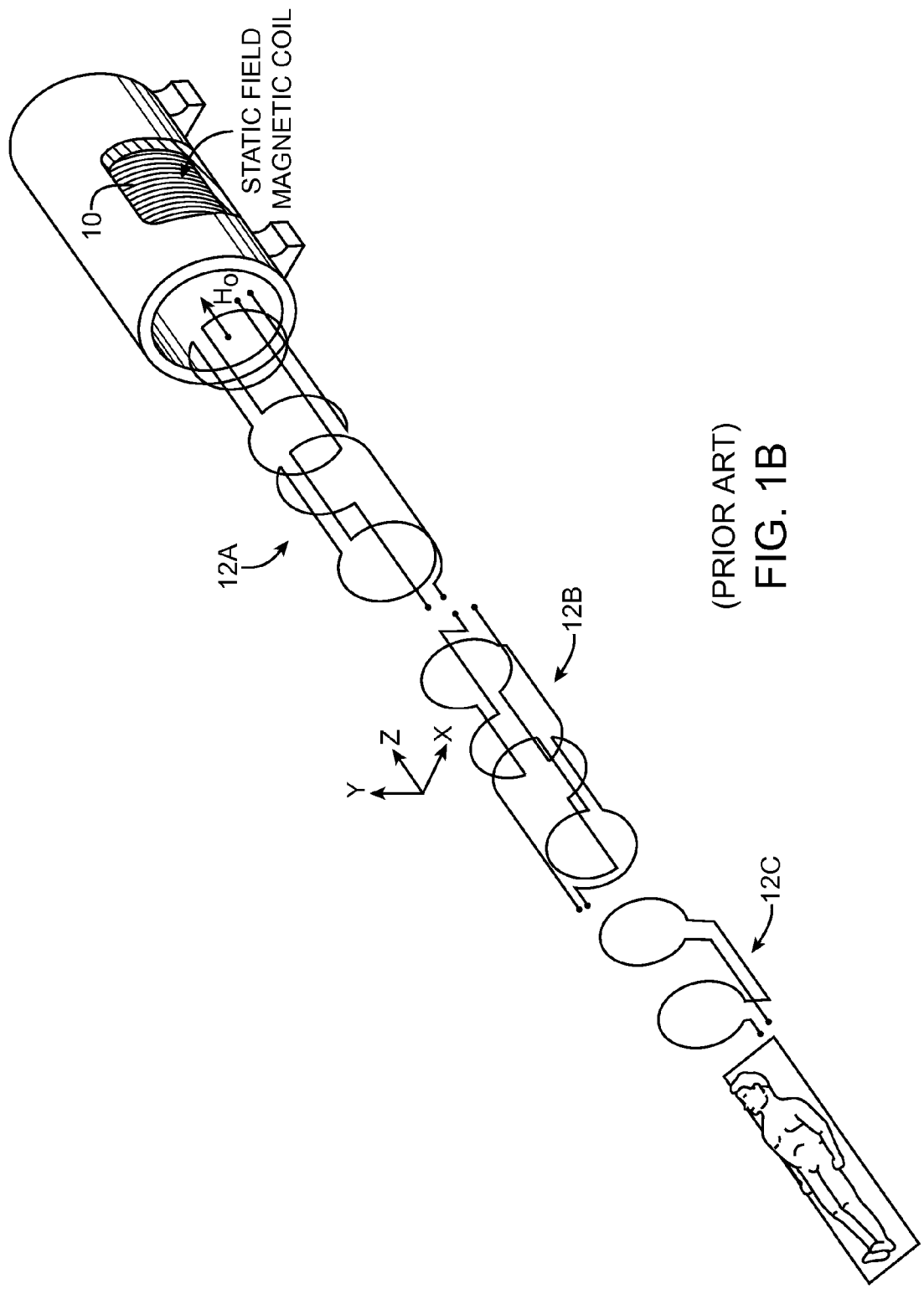
FIG. 1B schematically illustrates gradient coils of a prior MRI system.
Figure 1C:
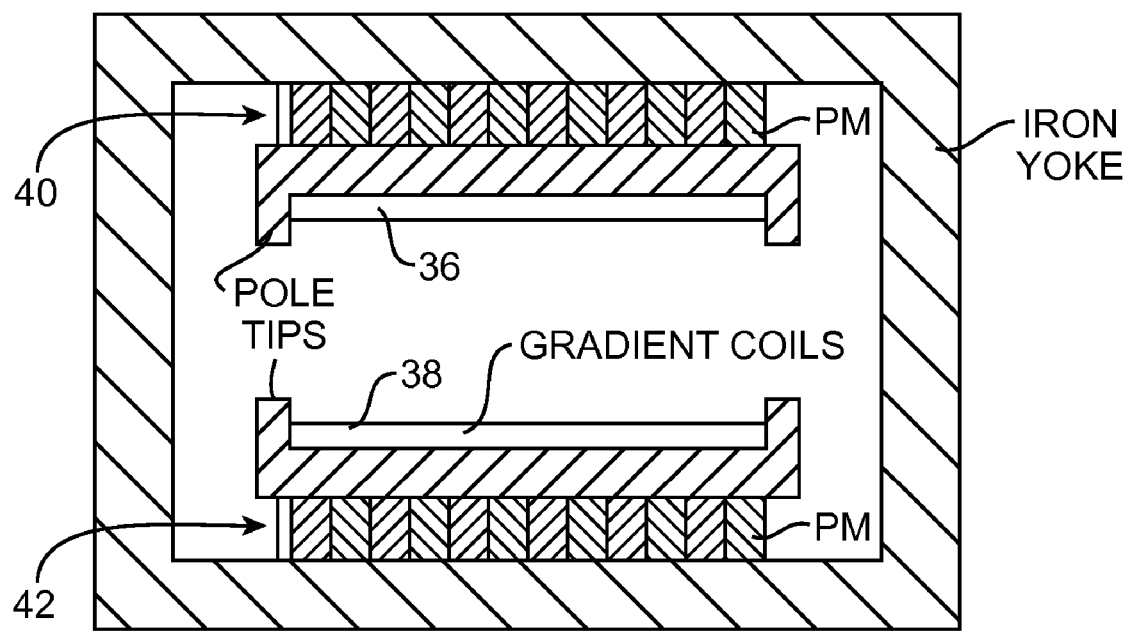
FIGS. 1C to 1E schematically illustrate iron yoke magnets of prior MRI systems.
Figure 1D:
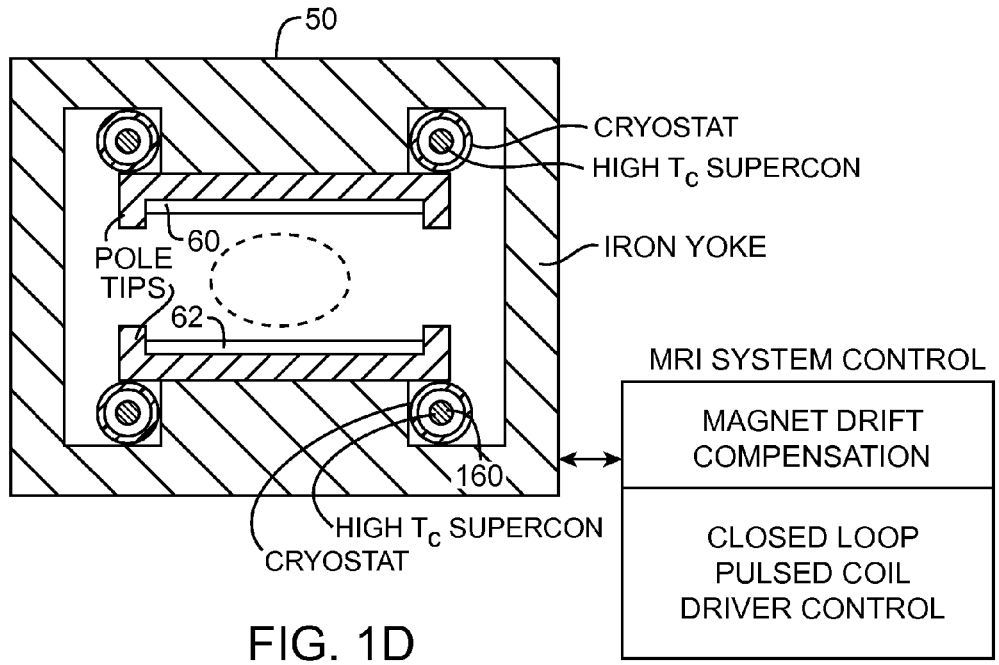
Figure 1E:
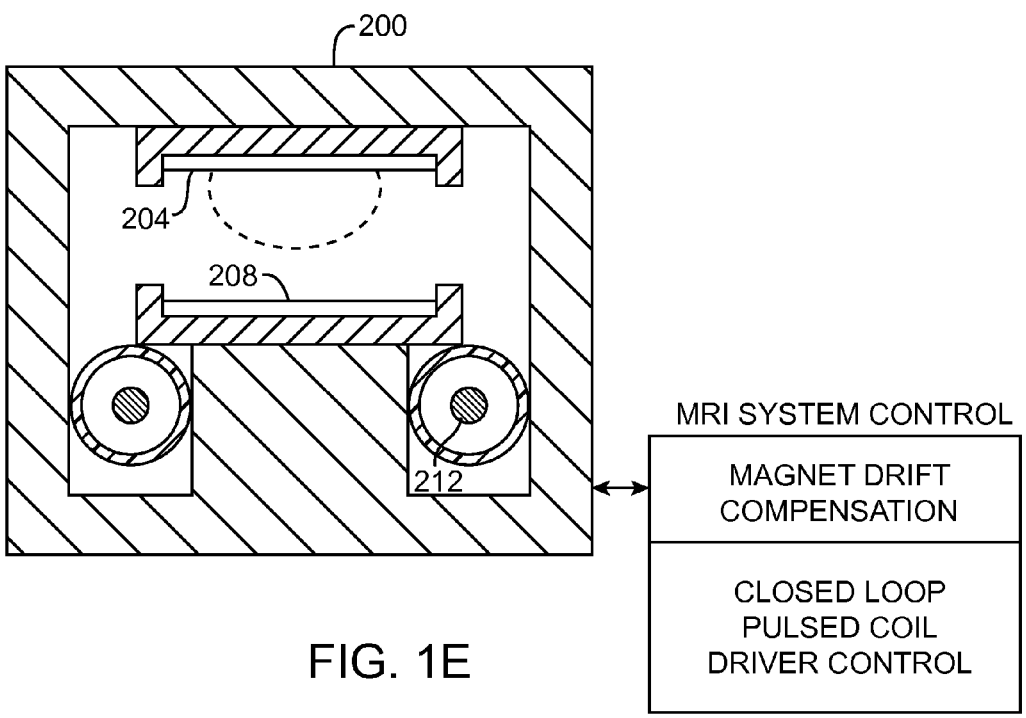
Figure 1F:
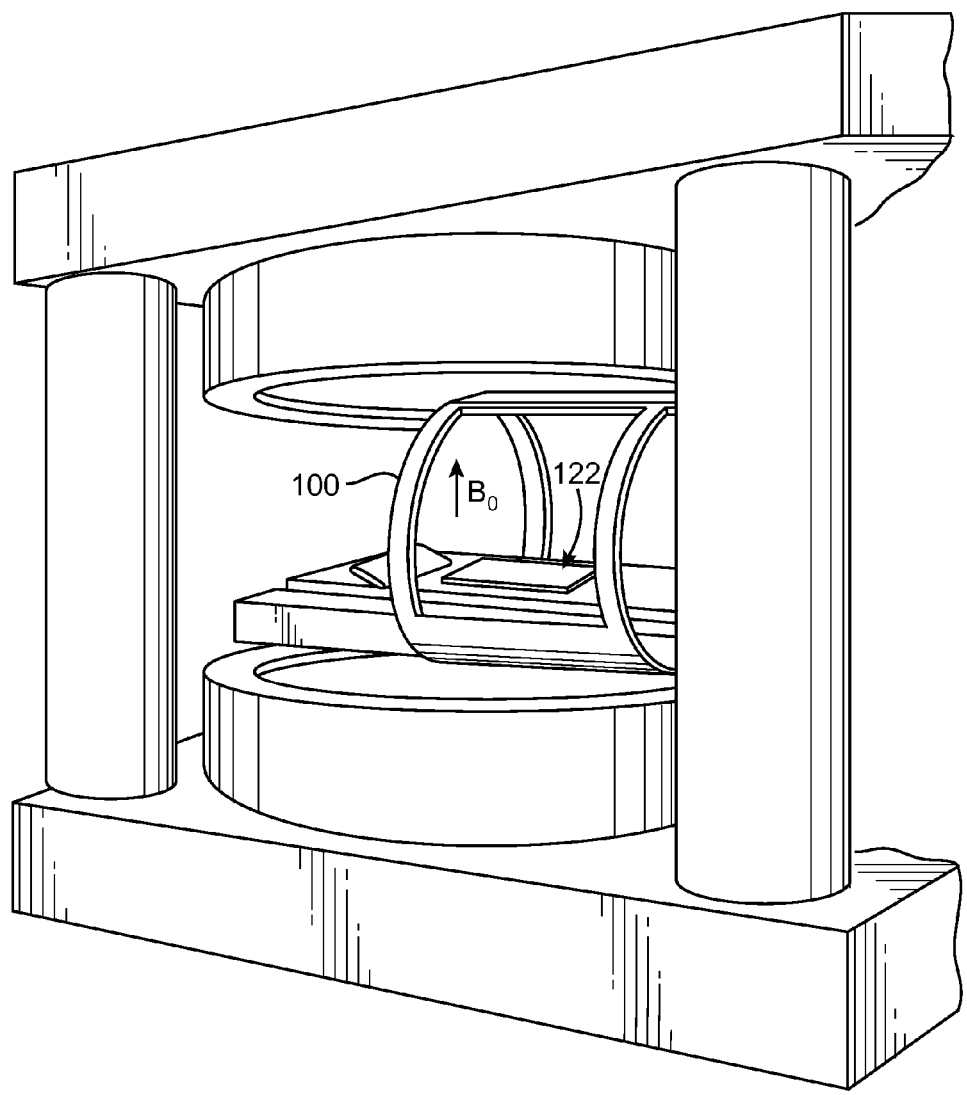
FIG. 1F schematically illustrates a prior RF receive coil distinct and decoupled from an RF transmit coil.

Referring now to FIG. 1A which schematically illustrates a prior art MRI system employing a gradient coil. As those skilled in the art will appreciate, the FIG. 1 depiction is schematic and omits much complexity so as not to obfuscate important features. In such a typical MRI system, a stable uniform and static magnetic field $B_o$ may be created by a main solenoidal magnetic 10 (e.g., a cryogenic superconducting electromagnet). A set of three gradient coils 12 can be used for creating gradients in the main magnetic field along each of three mutually orthogonal coordinate directions x, y, z, respectively. A radiofrequency ("RF") coil 14 can be tightly coupled to an interior image volume (e.g., containing a patient's head) for transmitting and receiving RF signals into and out of the image volume. FIG. 1B shows a schematic of gradient coils for a cylindrical magnet of the prior art, for example U.S. Pat. No. 4,607,225, the full disclosure of which has been previously incorporated herein by reference. The gradient coil includes three gradient coils 12A, 12B and 12C for generating magnetic field gradients along the x, y, and z axis respectively. Other configurations for magnets and gradient coils are possible. For example, FIG. 1C shows a cross-section of an iron yoke magnet with permanent magnet drivers 40 and 42 incorporating flat gradient coils 36 and 38, as described in U.S. Pat. No. 5,250,901, the full disclosure of which has been previously incorporated by reference. In yet another configuration shown in FIGS. 1D and 1E, symmetrical 50 and asymmetrical 200 iron yoke magnets are driven by superconducting coils 160 and 212, respectively, and also incorporate flat gradient coils 60 and 62 and 204 and 208, for example as described in U.S. Pat. No. 5,250,901. The RF transmit and RF receive functions need not be incorporated into a single coil. As shown in FIG. 1F an RF receive coil 122 is distinct and decoupled from an RF transmit coil 100, for example as described in U.S. Pat. No. 5,386,191, the full disclosure of which has been previously incorporated by reference.

Referring again to FIG. 1, the RF coil 14 (or in some applications separate transmit and receive RF coils) can be connected to suitable transmit and receive RF circuitry 18 as will be appreciated by those of ordinary skill in the art. The set of gradient coils 12 are individually driven by the usual Gx, Gy, and Gz gradient drivers 20, 22, and 24. The sequencing of the gradient drivers and of RF transmit/receive operations is typically controlled by a preprogrammed sequence controller 26 which is, in turn, under control of a human operator via console 28 and the remainder of the typical MRI system (e.g., processor 30 which ultimately receives RF signal responses from the image volume and converts them into a suitable visual image that may be displayed, photographed or otherwise recorded for medical diagnostic purposes).

In such whole-body MRI systems as those described above, the dimensions of the main magnet and of the associated gradient coils can utilize relatively large scale geometry for a number of reasons. First of all, the system is often large enough to accommodate a human body (or at least the portion of the human body that is to be imaged). But, perhaps even more importantly, to obtain the desired uniformity, linearity and/or reproducibility of magnetic fields within the image volume, the image volume can often include a relatively small and limited portion of the entire volume bounded by the above MRI structures. The size of such systems can affect hardware costs as well impose complex and expensive siting requirements.

The gradient coils can be used for encoding position information into NMR signals so that the position of the NMR signal source can be determined, for example U.S. Pat. No. 4,318,043, issued to Crooks, et al. on Mar. 2, 1982, and entitled "Method and apparatus for rapid NMR imaging of nuclear densities within an object", the full disclosure of which is incorporated herein by reference. Thus, an MRI system can benefit from the use of a robust gradient system capable of fast and strong gradients. Even with robust gradient systems, the gradient subsystem can, and often does, limit the performance of an MRI unit.

There are clinical applications (including characterizing of vulnerable plaque, characterizing tissues adjacent body lumens and cavities, characterizing tissues adjacent skin, and the like) where it would be beneficial to obtain images with a small field-of-view (FOV) and very high spatial resolution. The speed and strength of known MRI gradient fields, and the available peak RF power, can limit spatial resolution. In a whole body imaging system, even though the FOV of interest may be small (on the order of a millimeter), the gradient and RF fields are established over the whole volume of the unit, in some instances larger than 50 cm. The physical requirements for accomplishing a smaller FOV, high resolution, and reasonable speed using known MRI structures can be extensive.

A further limitation can be imposed by the reception coil: Although a signal may be desired from only a small volume in the subject, an external coil is sensitive to all of the tissue within its field, so that noise is received from a very large volume as compared to the volume of interest can degrade signal-to-noise (S/N) levels. U.S. Pat. No. 5,699,801, issued to Atalar, et al. on Dec. 23, 1997, and entitled "Method of internal magnetic resonance imaging and spectroscopic analysis and associated apparatus; and U.S. Pat. No. 6,263,229, issued to Atalar, et al. on Jul. 17, 2001, and entitled "Miniature magnetic resonance catheter coils and related methods," (the full disclosures of which are incorporated herein by reference) seek to better match coil FOV and the desired FOV, and selected structures and methods of these known techniques may be used with those described herein. Such Intravascular MRI (WMRI) can utilize an RF coil that is inserted via a catheter into the artery, affording a close-up, 'inside-out' MRI view of the arterial wall. IVMRI may offer a potential solution for acquiring high-quality images of arterial plaque in ex vivo applications. As more fully explained in an article by Correia, et al., "Intravascular magnetic resonance imaging of aortic atherosclerotic plaque composition," *Arterioscler Thromb Vasc Biol.*, 17, 3626 (1997), IVMRI applied to human aortic specimens may also have an ability to characterize plaque composition via T2-weighted imaging, and to measure atherosclerotic burden in terms of plaque size. Pulse sequences taking advantage of differences in biochemical structure of plaque components, including magnetization transfer (MT), may also show quantitative differences in signal properties between fibrous cap, lipid, and calcium in human carotid endarterectomy specimens (as can be more fully understood with reference to Rogers, et al. "Characterization of Signal Properties in Atherosclerotic Plaque Components by Intravascular MRI," *Arterioscler Thromb Vasc Biol.*, 20, 1824 (2000)). Agreement between MRI using an intravascular coil and histopathology for different components of the lesion (possibly including a lipid core and fibrous cap) using IVMRI may be understood from Worthley et al., "A novel nonobstructive intravascular MRI coil: in vivo imaging of experimental atherosclerosis," *Arterioscler*

*Thromb Vasc Biol.*, 23, 346 (2003). It may similarly be possible to differentiate hydrogen in water vs. lipids by spectral distribution.

IVMRI may be hampered by several challenges. For example, a close match between coil and internal blood vessel diameter (which might help to prevent signal fall-off in the radial direction) can make it difficult to advance the catheter in the blood vessel. Also, axial resolution can be limited resulting in repeated imaging along the arterial length. Image quality can also be reduced as the IVMRI coil rotates with respect to the axis of the external magnetic field, which can present problems for imaging tortuous coronary arteries.

Magnetoresistive Sensors for NMR and/or MRI

Magnetoresistive sensors are thin-film solid-state devices that can measure very small magnetic fields from DC to 1 GHz with high sensitivity, low noise, and low power. Sensors based on the anisotropic or giant magnetoresistive effect (AMR and GMR, respectively) can have magnetic field detectivity on the order of $10^{-10}$ T/$\sqrt{Hz}$. SQUID devices may have detectivity several orders of magnitude better, but can require cooling and other bulky ancillary electronics, and may be unsuitable for intra-arterial scanning in some instances. Furthermore, whereas SQUIDS are flux sensitive, magnetoresistive sensors are field sensitive; i.e., the sensitivity can be independent of sensor size. We have exploited these properties of magnetoresistive sensors to achieve magnetic field images. We have fabricated one or two-dimensional arrays of small AMR sensors onto silicon using standard photolithography techniques. These arrays provide magnetic field images that we have used in applications such as hairline crack detection in metals, and diagnosing small electronic components on printed circuit boards, for example see co pending U.S. application Ser. No. 11/120,510, filed on May 5, 2005. Arrays made from sensors of submicron dimensions can provide microscopic images without the loss of signal-to-noise ratio that results when scaling down a conventional flux-sensitive sensor such as a wire coil or SQUID. Sensor arrays can also be constructed based on GMR sensors, for example as described in U.S. Pat. No. 6,150,809 and U.S. Publ. No. 2003/0029345, the full disclosures of which are incorporated herein by reference.

Figure 2:
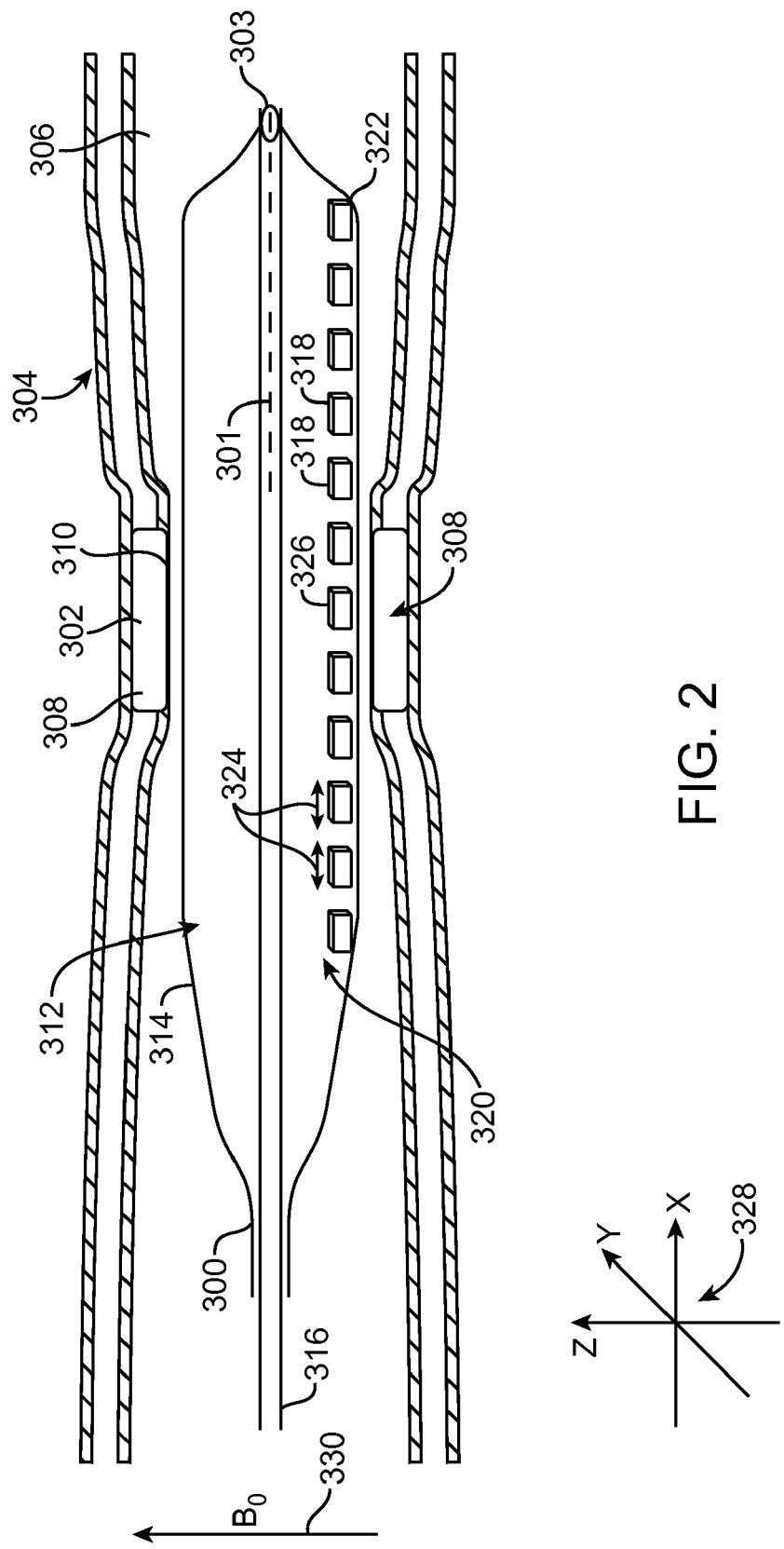
FIG. 2. shows intravascular MR probe for scanning vulnerable plaque, in accordance with an embodiment.

Referring now to FIG. 2, an intravascular MR device which includes a probe 300 for scanning a vulnerable plaque 302 is shown in accordance with an embodiment. Probe 300 includes a distal end 303 and can include an axis 301 along which the probe can be advanced to position the probe near plaque 302. As shown in FIG. 2, probe 300 is positioned in a lumen 306 of an artery having an arterial wall 304. Vulnerable plaque 302 includes a lipid pool 308 and a fibrous cap 310. The device includes an array 322 of AMR sensors 318 inside a balloon catheter 312 to detect the proton MR signal of the arterial wall. Balloon catheter 312 includes an expandable member, for example balloon 314, and a catheter 316. A row 320 of magneto resistive sensors is attached to balloon 314. Each sensor occupies an array site 326 on probe 300. Balloon catheter 312 can include a double layer balloon with the row of magneto resistive sensors positioned between the two balloon layers, and the sensors can be supported by and electrically connected to a polyimide printed circuit board which is also positioned between the layers of the double layer balloon. While many rows of magneto resistive sensors can be used, for example 10 rows, only one row of magnetoresistive sensors is shown in FIG. 2 for clarity. Additional rows of magnetoresistive sensors can be positioned circumferentially around probe 300 at angular orientations about axis 301 to separate the field of view of the rows sensors. For example four rows of sensors can extend axially along probe 300 and be positioned circumferentially around probe 300 in 90 degree increments.

Each AMR sensor is sensitive to a magnetic field along a surface plane of the sensor, and if that magnetic field is sufficiently strong, the sensor can saturate. As a consequence, a static $B_o$ field 330 can be oriented orthogonally to the plane of the device to avoid saturation. Thus, the probe can be used in the field of an external magnet as described above if the proper relative orientation is maintained. For example, an XYZ coordinate reference system 328 shows the Z axis parallel to the static $B_o$ field, and each sensor plane 324 located parallel to a plane defined by the X and Y axes, so that the static $B_o$ field is orthogonal to the sensor planes.

Figure 2A:
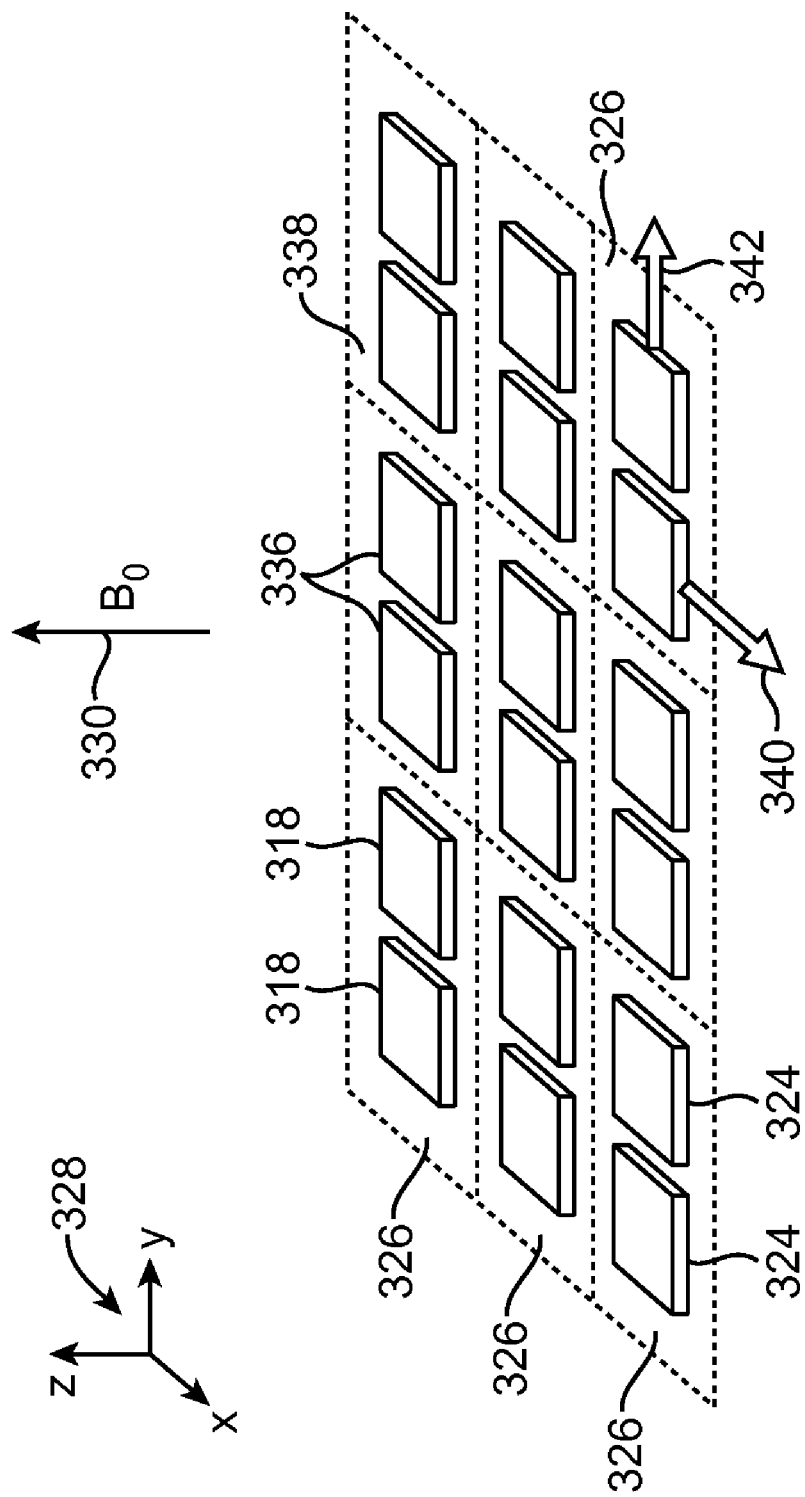
FIG. 2A shows sensor pairs arranged in a 3×3 array for quadrature detection of the MR signal.

FIG. 2A shows sensor pairs arranged in a 3×3 array 338 for quadrature detection of the MR signal. Each array site 326 includes a pair 336 of sensors 318. A first sensor of the pair has a first sensitive direction 340, and a second sensor of the pair has a second sensitive direction 342. The sensitive directions of the two sensors at each array site are orthogonal to one another, lying parallel to the x- and y-axes, and are also orthogonal to the static magnetic field ($B_o$) that lies parallel to the z-axis.

In a preferred embodiment, the magnet, which can include an electromagnet or permanent magnet, can be included in the probe, as described in more detail below with reference to FIG. 3. Similarly, an external RF transmit coil can be used. In a preferred embodiment, an integrated RF coil is included in the probe and connected to an RF power supply by a cable. An integrated RF coil can be inductively coupled to an external coil which is in turn connected to the RF power supply. Because the sensors are mounted on (an in some cases inside) the balloon, the probe can scan arteries with a wide range of diameters with gentle inflation.

The AMR sensors are sensitive to magnetic fields along the plane of the sensor as described above. In preferred embodiments, the AMR sensors are sensitive to magnetic fields along a single direction in the sensor plane. Because the sensors can be sensitive to fields along one direction only it is possible to place two sensors at each array site, either side by side or stacked, with the sensitive directions of the two sensors at the array site aligned orthogonal to each other, and in this manner detect the NMR signal in quadrature, which can yield a 40% improvement in signal-to-noise. While orthogonal orientation of the sensitive directions of each sensor pair at a probe site can be preferred, in some embodiments the NMR signal can be still detected in quadrature at the probe site if the sensitive directions of each sensor pair are oriented at angles, for example oblique angles. An intensity of each NMR signal measured in quadrature with each pair of sensors at a probe site can be directly mapped to a location in an NMR image substantially dependent on the site on the probe. Although images can be formed by a direct mapping of the sensor signal from a probe site to a specific location in the display matrix, it is also possible to apply well known smoothing, sharpening and filtering algorithms to the images, so that the information at any one location in the image results from the weighting of information provided by a plurality of sensors.

The design is scalable; thus, devices in a range of geometries can be constructed for application in various sized vessels and body cavities. Additionally, the number of sensors used can be scaled from a few sensors to hundreds of sensors.

Figure 3:
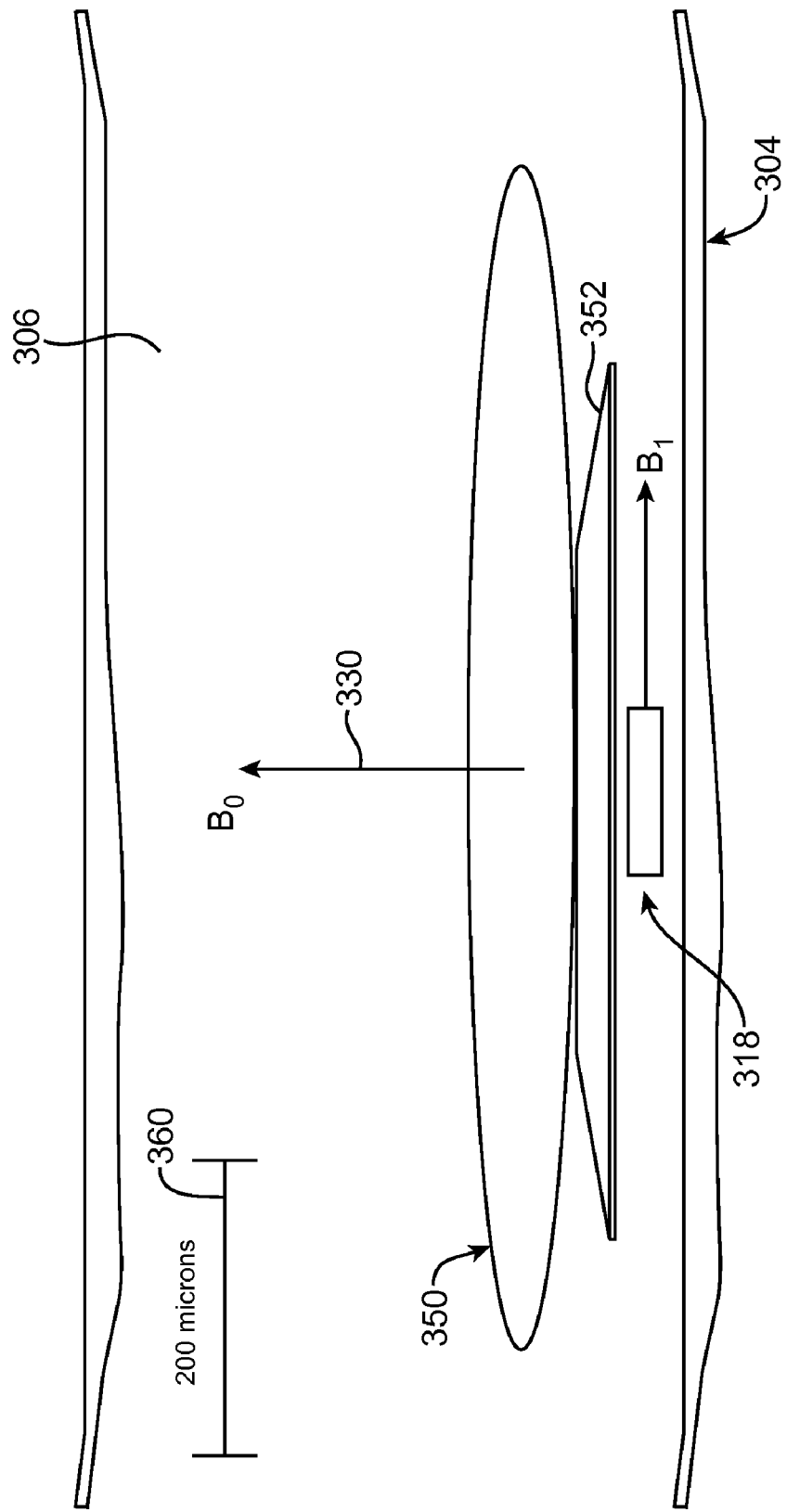
FIG. 3 shows a close-up schematic of single AMR sensor, a magnet, and an RF transmit coil.

Referring now to FIG. 3, a close-up schematic of a single AMR sensor 318, magnet 350, and RF transmit coil 352 are shown. Magnet 350 produces the static $B_0$ field. Magnet 350 can be an electro or permanent magnet. Coil 352 produces the radiofrequency $B_1$ field. Sensor 318 is sensitive to the magnetic field produced by coil 352, and as is the practice in NMR, the sensing electronics for sensor 318 can be gated off during transmission by coil 352.

A scale 360 having a size of 200 microns shows the single sensor to have a size of approximately 100 microns. Various combinations of magnets and sensors are possible. For example, a single magnet can be positioned with a sensor array. In another embodiment, several magnets are located near the sensors, so that each magnet is positioned in proximity to at least one sensor.

Figure 3A:
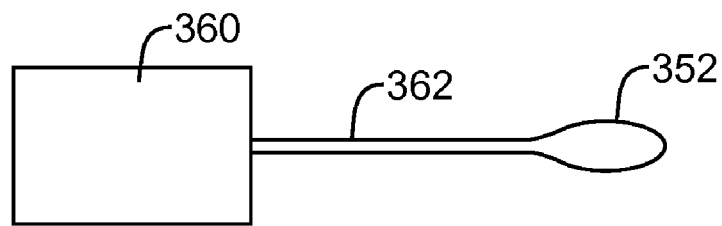
FIG. 3A shows an RF coil conductively coupled to a power source.

FIG. 3A shows an RF coil conductively coupled to a power source. A power source 360 provides electrical energy to coil 352. A conductor 362 conductively couples the RF coil 352 to the power source 360.

Figure 3B:
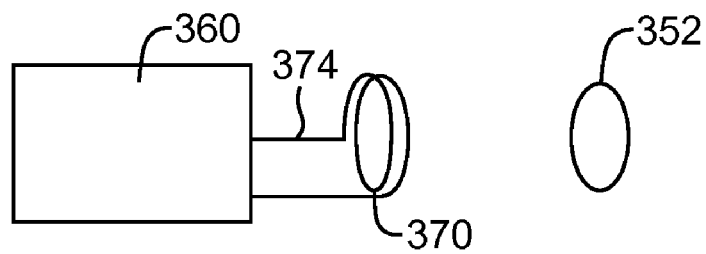
FIG. 3B shows an RF coil inductively coupled to a power source.

FIG. 3B shows an RF coil inductively coupled to a power source. An external inductor 370 is conductively coupled to power source 360 with an external conductor 374. External coil 374 couples directly to internal coil 352, thereby providing power to internal coil 352.

Figure 3C:
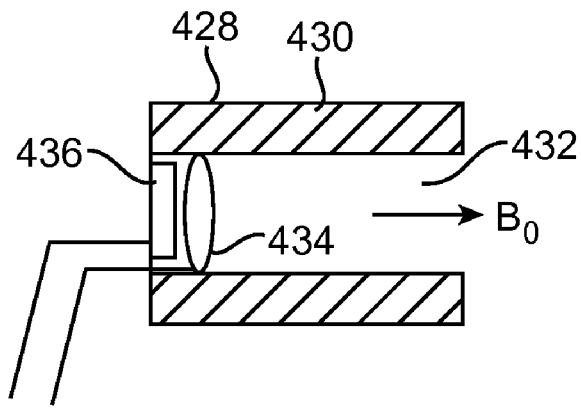
FIG. 3C shows a probe with a cavity formed therein to position the material in the cavity near the sensors.

FIG. 3C shows a probe 428 with a structure 430 cavity 432 formed therein to position the material in the cavity near AMR sensors 436 and coil 434 as described above. The structure 430 can be a magnet having a bore formed therein to define cavity 432. Such a probe configuration can be useful for measuring extruding tissue and fluids within cavity 432. In some embodiments, the probe can be used to measure NMR signals from fluids outside the body, for example ground water and chemical contamination of ground water.

Sensor Design and Fabrication

Figure 4:
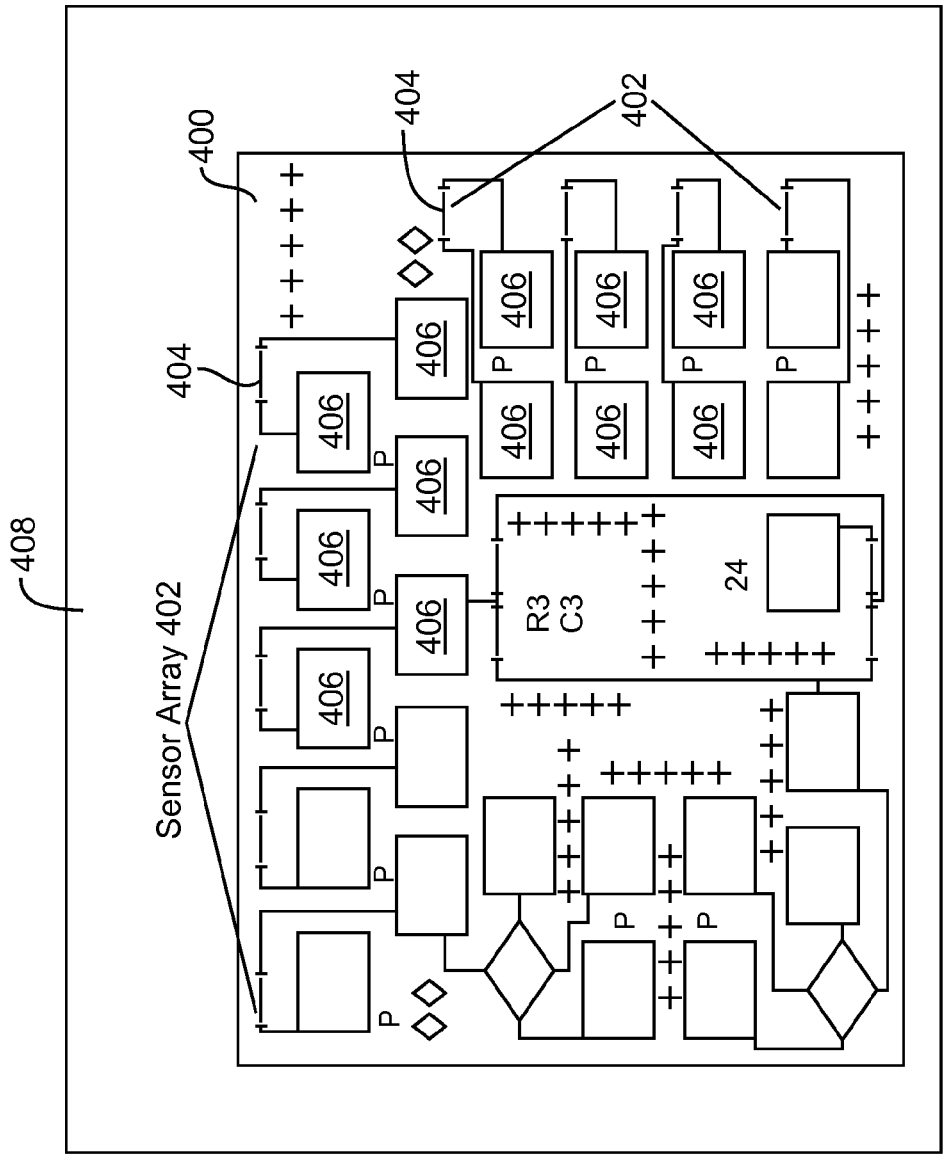
FIG. 4 shows AMR sensors on a 1 mm silicon die having several arrays of barber-pole sensors in various configurations.

FIG. 4 shows several AMR sensors on a 1 mm silicon die 400 having several arrays 402 of barber-pole sensors 404 in various configurations. Pads 406 shown as large squares are 100 micron pads for bonding, for example wire bonding to the sensors. AMR technology provides the capability to fabricate microscopic arrays of magnetic field sensors on an intravascular MRI probe. AMR sensors can be made from a thin strip of permanent magnetic material (permalloy), and can be fabricated using standard photolithographic techniques on silicon substrates as shown in FIG. 4. In general terms, with 'suitable magnetic biasing', a quasi-singular domain exists along the anisotropy (easy) axis of the permalloy, generally the long axis. When an external field is applied in the plane of the permalloy, the domains rotate slightly, changing the permalloy's resistance. If a constant current is applied to the magnetoresistor, then the voltage across the sensor is proportional to, and serves as a sensitive measure of, the external magnetic field. The aforementioned 'suitable magnetic biasing' can be provided by locally modifying the direction of the applied constant current. With barber-pole type AMR sensors, thin aluminum shunts can be deposited at 45 degree angles along the permalloy strip, giving this sensor it name. Zigzag sensors can rely on a modified corrugated shape of the permalloy itself to provide the bias field, and can be scaled to nanometer dimensions. Barber-pole and zigzag sensors can be sensitive to a magnetic field applied perpendicular, and parallel to the applied current, respectively.

Newer magnetoresistive technologies include GMR (giant) and TMR (tunneling). GMR (giant magnetoresistive) sensors. Although more difficult to fabricate, these may have up to ten-fold greater sensitivity at frequencies above 10 kHz.

Referring again to FIG. 4, the sensor array can be mounted to a flexible printed circuit board (PCB) 408 made from any flexible substrate material, for example polyimide. While a 1 mm rectangular silicon die 400 is shown, the sensor array can be any size or shape, and several dies can be mounted to a PCB to provide a desired number of sensors on the probe as described above. Magnets and coils as described above can be connected to and supported by the flexible PCB located on the probe, for example between the two balloon layers as described above.

Comparison of Magnetoresistive Sensors with Wire Coils and SQUIDS

For the anisotropic magnetoresistive (AMR) sensors, the major noise source can be white noise (Johnson noise). At frequencies greater than 1 kHz, the noise spectrum can be flat. In GMR devices, 1/f noise can be important even above 1 kHz.

At "mid" and "high" field NMR frequencies (>5 MHz), patient noise may dominate any 1/f noise, for both AMR and wire coils, but it is important to note that, for the relatively small spatial scales that are considered here, the Johnson noise from the AMR sensor or wire coil will dominate both the magnetic patient noise and the 1/f noise.

The following is a comparison of SNR of magnetoresistive sensors with a similar sized-wire coil. Note that the two coils' noise voltages can be approximately the same; the big advantage of AMR sensors can be their much larger output, their reduced frequency dependence, and the fact that they are not flux-dependent.

AMR sensors possess signal-to-noise characteristics far surpassing wire-wound coils of similar dimension. Consider a single loop copper coil of radius 80 microns (fabricated on a silicon wafer) with a typically-sized trace width 10 μm and thickness 100 nm. The resistance at 4 MHz should be approximately 3 ohms, resulting in a noise voltage of $0.25$ nV/$\sqrt{Hz}$. The signal induced in this coil by a small volume of transverse nuclear magnetization may be proportional to frequency, the nuclear magnetization, and by the reciprocity principle, the field produced per unit current by the coil. If the nuclear magnetization is a 10 μm thick, 160 μm wide slab of water protons in a 100 mT field, located just beneath the coil, the signal induced in the wire coil is calculated to be approximately 2.5 pV. Thus the SNR for the wire coil can be approximately $0.01/\sqrt{Hz}$.

Compare the wire loop coil with a barber-pole sensor, which can have a resistance of 60 ohms, producing a measured noise floor of 1 nV/$\sqrt{Hz}$, and a measured sensitivity of 8 V/T. The signal output from the same slab at 100 mT would be 8 nV, resulting in a SNR of $8/\sqrt{Hz}$, nearly 1000 times better than the wire coil. Also, unlike wire coils, magnetoresistive sensors can be dependent upon field, not the time rate of change of field, making their sensitivity less frequency dependent.

SQUIDs (superconducting quantum interference devices) may provide the gold standard for super-sensitive magnetic field detection, and can be capable of sensitivity of 1 fT/$\sqrt{Hz}$. One drawback with SQUIDs can be the need for cryogenic cooling and ancillary instrumentation. Furthermore, SQUIDs can be flux sensitive whereas magnetoresistive devices can be dependent on magnetic field, independent of their size. In fact, AMR devices may become competitive with SQUIDS for areas smaller than 10 μm2. Thus, magnetoresistive sensors can provide a combination of sensitivity, small size, and scalability that can make them the best choice for an array MRI probe.

MRI Using a Miniature Static Field

The axial magnetic field, $B_z$, due to a circular loop coil in the x-y plane is proportional to the current and the number of turns, and inversely proportional to the coil radius. The $B_z$ field, as defined in the context of MRI as the $B_0$ field, can vary with depth in a well understood manner, dropping with the cube of distance once a few radii away from the coil. Thus, a major issue with using a planar coil to generate $B_0$ can be the substantial field inhomogeneity in the axial direction.

Fortunately, the morphology of the arterial wall is amenable to a planar coil. The thin fibrous cap in rupture-prone plaque can extend less than 65 μm below the intimal surface, separating the lumen from a large lipid core extending some hundreds or thousands of microns into the wall. Thus, an IV MR probe capable of imaging several hundred microns deep for a typical coronary lesion (less deep for smaller arteries) can identify vulnerable plaque.

Figure 5:
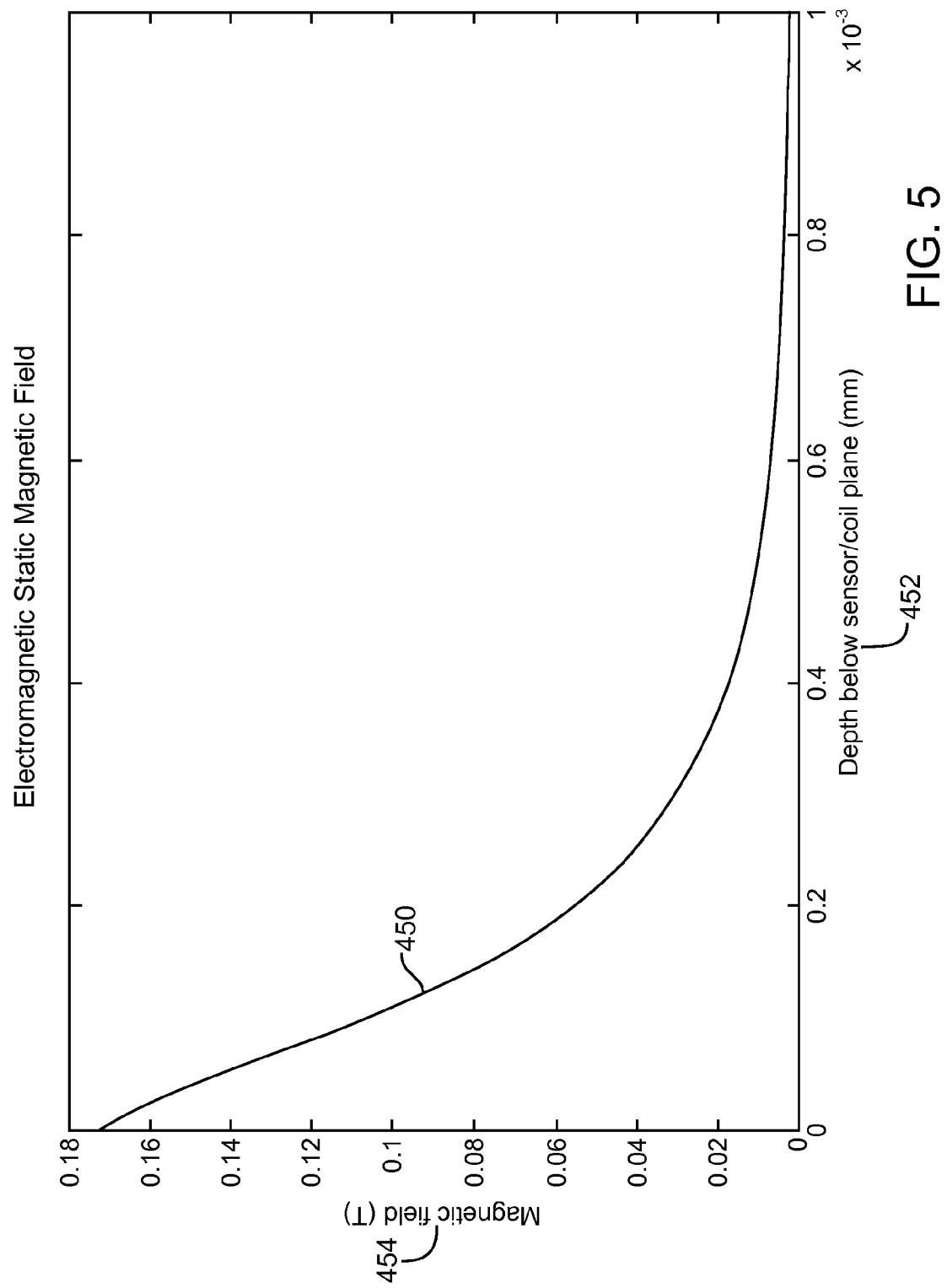
FIG. 5 shows magnetic field profile as a function of depth below the planar electromagnetic coil for the intravascular MR probe. The resistive losses from this coil can be 5 W.
Figure 5A:
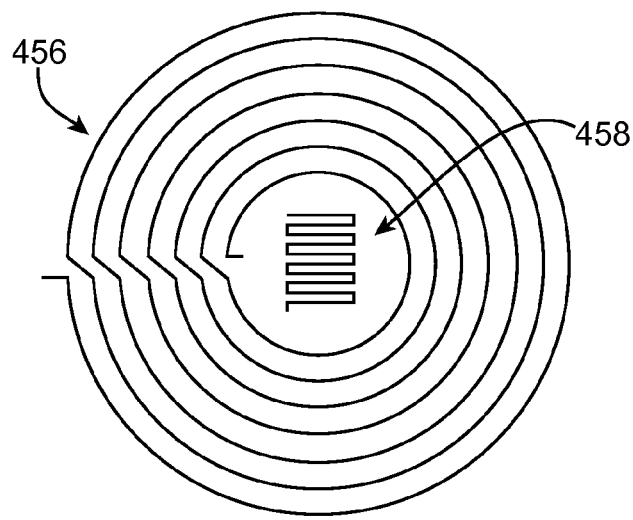
FIG. 5A shows basic schema of a bi-layer spiral static $B_0$ magnetic field coil and a serpentine AMR sensor. A 700 µm diameter spiral coil comprising 100 turns in two layers produces the magnetic field profile shown in FIG. 5 with approximately 5 W of Joule heating. A serpentine AMR sensor with serpentine geometry with overall dimensions of approximately 100×120 µm fits in the interior of the coil. The detectability of the coil and sensor is shown in FIG. 6.

FIG. 5 shows a profile 450 of the calculated $B_o$ field 454 as a function of depth 452 below a bi-planar electromagnetic coil each plane comprising 100 turns in a spiral pattern with a current capacity of 300 mA. The $B_o$ field for a 700 μm diameter spiral coil can be seen to be greater than 0.05 T down to a depth exceeding 200 μm. These coils can be readily fabricated by depositing 100 turns in 2 layers of 50 micron thick gold separated by a 1-2 micron insulating layer onto a semiconductor substrate using standard photolithographic techniques (FIG. 5A). Joule heating of the coil in this example is approximately 5 W. Although it decreases rapidly with depth, the magnetic field $B_o$ thus generated is sufficient for MR imaging of the wall. For stability, the current source can utilize as feedback a signal, output by the NMR signal detection card, proportional to the baseband RF frequency. This will create a field-lock loop, whereby the current source output is continuously adjusted to provide a steady current, and thus a steady $B_o$ field and NMR frequency. DC magnetic field stability may be provided on order of 0.1 ppm per hour (hence, as stable as a superconducting magnet) with little jitter. The AID is capable of detecting sub-Hertz (mHz) changes in MHz RF signals, thus the field-lock system can provide the desired precision feedback signal for a very stable, constant static field.

Similarly, a permanent magnet of the same dimension as a coil can produce a stronger field if made of a material such as Neomax (TM). Other materials that are useable are Samarium-Cobalt, Alnico, and so on. The permanent magnet can be inherently stable. Neomax is particularly insensitive to temperature changes, which, in the body can be quite constant. Permanent magnets can eliminate the need for power supplies and cabling and do not produce heat. They can afford more compact and safer devices.

FIG. 5A shows basic schema of a bilayer spiral static $B_o$ magnetic field coil 456 and a serpentine AMR sensor 458. While several embodiments of the magnetic field coil are possible, a 700 μm diameter spiral coil consisting of 100 turns in two layers can produce the magnetic field profile shown in FIG. 5 with approximately 5 W of Joule heating. While many AMR sensors can be used, a serpentine AMR sensor with serpentine geometry with overall dimensions of approximately 100×120 μm can fit in the interior of the coil as shown in FIG. 5A. The detectability of the coil and sensor is shown in FIG. 6.

Detection of Arterial Wall MR Signal Using a Magnetoresistive Sensor

The MR signal at the sensor may be proportional to the transverse nuclear magnetization precessing about $B_o$, and may also be dependent on the displacement vector from the magnetization to the sensor. As noted previously, the frequency dependence is via $B_o$. A calculation of the proton MR signal at the magnetoresistive sensor, presumed to be at the center of the static field coil, emanating from various depths along the axis of the coil may also be performed. The sample can be presumed to be water (nuclear susceptibility=3.1×10$^{-3}$ (A/m)/T). The nuclear magnetization following a 90° excitation pulse can be calculated for contiguous 10 μm thick slices, coplanar with the static coil, along the z-axis to a depth of 0.8 mm, with this slice thickness optionally being selected for RF considerations, as explained below. The magnetization can be calculated by integrating the effective surface and volume current densities over the 3D slice via the Biot-Savart law, as can be understood with reference to Lorrain, P., et al., "Electromagnetic fields and waves," 2nd edition, WH Freeman, San Francisco. p. 387 (1970).

Figure 6:
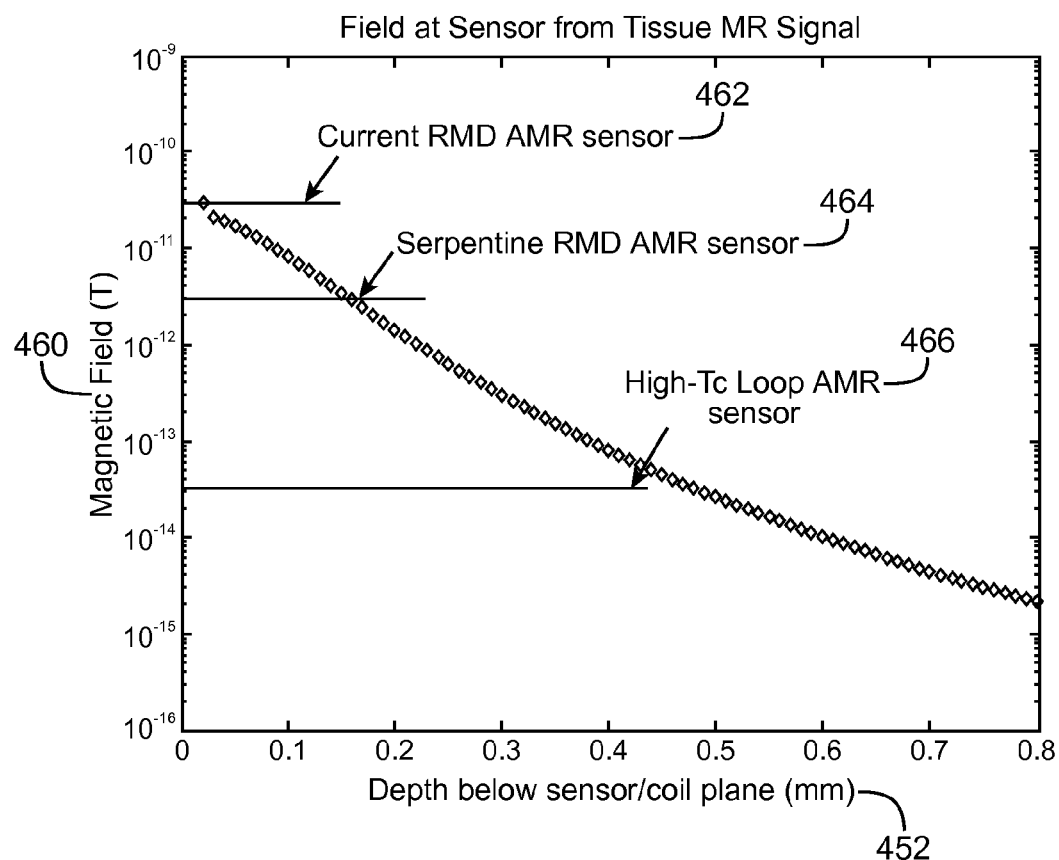
FIG. 6 shows calculated MR signal versus depth below the coil, along with detectability limits of various magnetoresistive sensors assuming averaging signal from 10 slices of 10 µm each and collecting data for 100 seconds.

FIG. 6 shows a calculated MR signal at the sensor 460 versus depth 452 below the coil. Included in the figure are detectability limits of various magnetoresistive sensors assuming collecting data for 100 seconds and averaging signal from 10 slices each 10 μm thick; since we are interested in detecting lipid behind the fibrous cap, a large signal-to-noise improvement (>3×) can be realized by integrating ten or more slices at depths below 65 μm. The detectability limits shown are a current AMR sensor detectability limit 462, a serpentine AMR sensor (FIG. 5A) detectability limit 464, and a high Tc Loop AMR sensor detectability limit 466. These calculations indicate that the $B_0$ coil will generate sufficient static field such that the arterial wall MR signal will be detectable using a magnetoresistive sensor at depths relevant for detecting vulnerable plaque. Our current magnetoresistive sensors can possess a noise floor of 1 nT/$\sqrt{Hz}$, or equivalently, 10$^{-10}$ T for a 100 second scan (worst case scenario). The MR signal is seen in FIG. 6 to vary from approximately 3×10$^{-11}$ T just below the sensor, to approximately 10$^{-11}$ T at 100 μm (a depth that is within the lipid layer), and then decreases further to approximately 10$^{-12}$ T at a depth of 200 μm. Thus, for a 100 second scan, the MR signal arising from a 100 μm deep lipid pool can be within the range of detection.

An approach to improving SNR can include an array of conducting loops that have a short constriction in the current path, so that the current density is increased at the constriction, proximal to which is placed a sensor. Using superconducting loop sensors, with over three orders of magnitude greater SNR, much greater depths can be probed; alternatively, the higher SNR could be traded for lower scan time, or simply for improved data quality. Where superconducting loops are not practical, normal conducting materials can be used, albeit with some loss in performance.

Arterial Wall MR Slice Selection Using the Intrinsic Gradient Field

Referring again to FIG. 5, the $B_0$ field of the planar intravascular electromagnet can be highly inhomogeneous, with gradients up to 500 T/m. This intrinsic static gradient can present a disadvantage, because unless precautions are taken, proton molecular self-diffusion in the gradient can severely reduce the MR signal. On the other hand, it can provide a means of slice selection in the z-direction, thus enabling discrimination of MR signal at various depths in the arterial wall. The following calculations demonstrate that a CPMG (Carr-Purcell-Meiboom-Gill) MR pulse sequence used with the intravascular device can achieve slice selection, minimize signal loss from diffusion in the intrinsic gradient, and provide T2- and diffusion-weighted tissue contrast, without the use of gradient coils.

Figure 7:
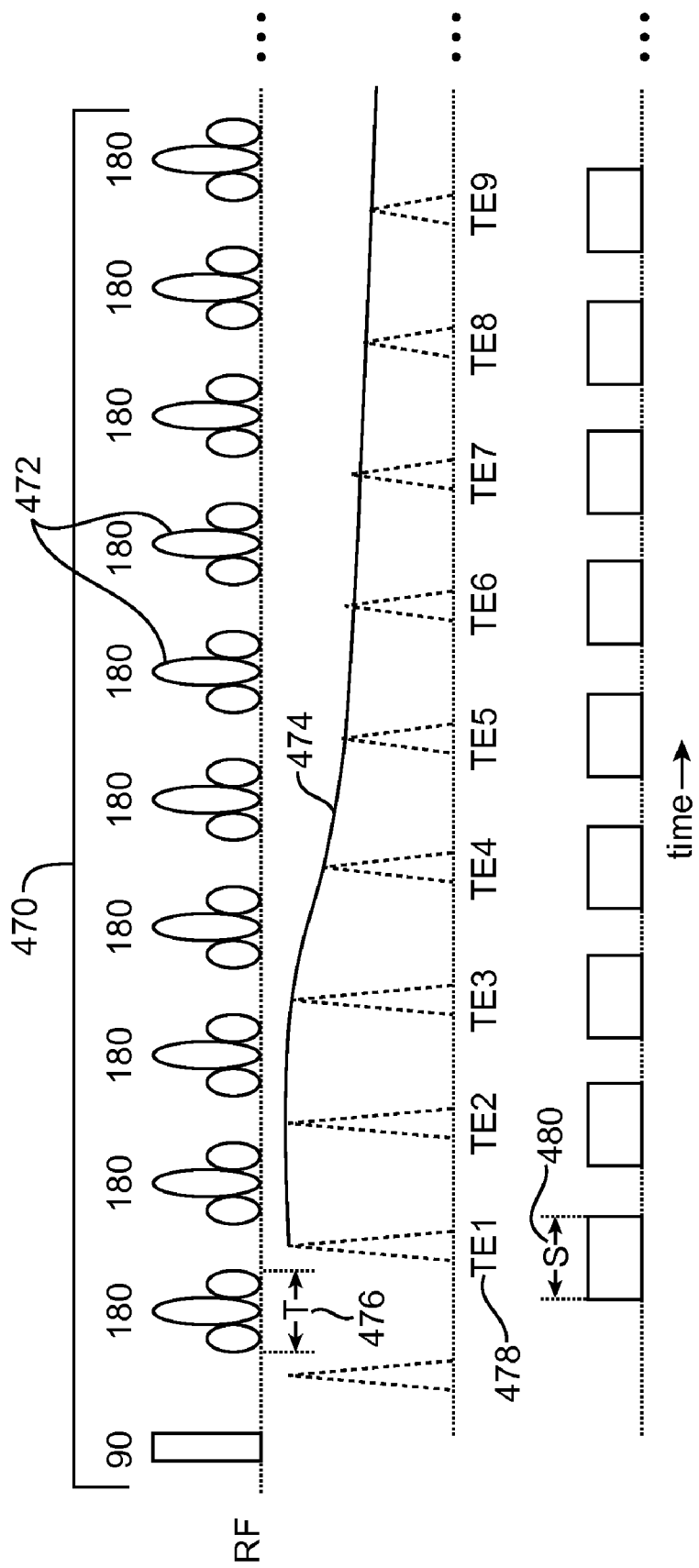
FIG. 7. Shows a Carr-Purcell-Meiboom-Gill (CPMG) MR pulse sequence with self-refocusing RF pulses at a specified carrier frequency in the intrinsic field gradient to provide slice selection.

FIG. 7 shows a CPMG MR pulse sequence 470 with self-refocusing RF pulses 472 at a specified carrier frequency in the intrinsic field gradient to provide slice selection. Using a large number of short, closely-spaced pulses can reduce diffusion attenuation. The echo envelope 474 reflects signal attenuation from both T2 and self-diffusion. The MR signal following a 90°-180° RF pair decays exponentially due to spin-spin relaxation as exp(−t/T2), where T2 is the relaxation time; it decays further due to self-diffusion in the presence of magnetic field gradients, G, as exp(−kt$^3$), where k is proportional to DG$^2$, and D is the diffusion coefficient. The signal attenuation due to the diffusion term can be reduced by a factor $n^2$ by collecting the MR signal using a train of n echoes, as illustrated in FIG. 7. The MR signal from water self-diffusing in a typical intrinsic gradient field (100 T/m) of the intravascular magnet collected at time t=10 ms would be attenuated by a factor of 3000 using a single 90°-180° RF pair. In contrast, for a train of n=100 echoes, the MR signal attenuates only by approximately 25% due to diffusion. It is noted that the lack of gradient pulses, which need time to stabilize, permits very close spacing of the refocusing pulses. It is also to be noted that for some purposes, it is sometimes useful to reduce the amplitude of the 180 deg refocusing pulses so that the rotation of the magnetization vector is less than 180 deg.

The CPMG pulse sequence can reduce diffusion attenuation in this way. However, there are tradeoffs among issues of diffusion signal loss, achievable slice thickness, RF power requirements, sampling rate, and echo time TE 478. The feasibility of producing the RF pulses and collecting the echoes on the desired time scale using the intravascular probe is demonstrated as follows. With n=100 echoes and a total echo train time TEn=10 ms, the pulse sequence can accommodate RF pulse width 476 of T=50 μs and echo sampling time 480 of S=50 μs. The bandwidth of the slice selective pulses is then 2/T=40 kHz, corresponding to a slice thickness on order of 10 μm. This is the slice thickness that we used to generate the MR signal in FIG. 6. Thicker can slices imply shorter pulses and higher RF requirements; for these reasons it can be advantageous to acquire many thin slices.

Contrast between normal tissue and lipid pools in vulnerable plaque may be provided by T2, diffusion, or both. Because the MR probe does not use gradient coils, the design of RF self-refocusing pulses, which do not require gradient pulses to correct the first order phase spread across the slice, can be of particular benefit. Mathematical frameworks described in an article by Rourke et al., "The inverse scattering transform and its use in the exact inversion of the Bloch equation for noninteracting spins," *J. Magn. Reson.* 99, 118 (1992) may facilitate calculation of self-refocusing pulses without gradient pulses. Existing solutions for performing high-resolution spectroscopy in an inhomogeneous field, using RF pulses matched to the static field profile, such as those in an article by Perlo et al., "High-resolution NMR spectroscopy with a portable single-sided sensor," *Science*, 308, 1279 (2005), may also be employed.

Figure 8:
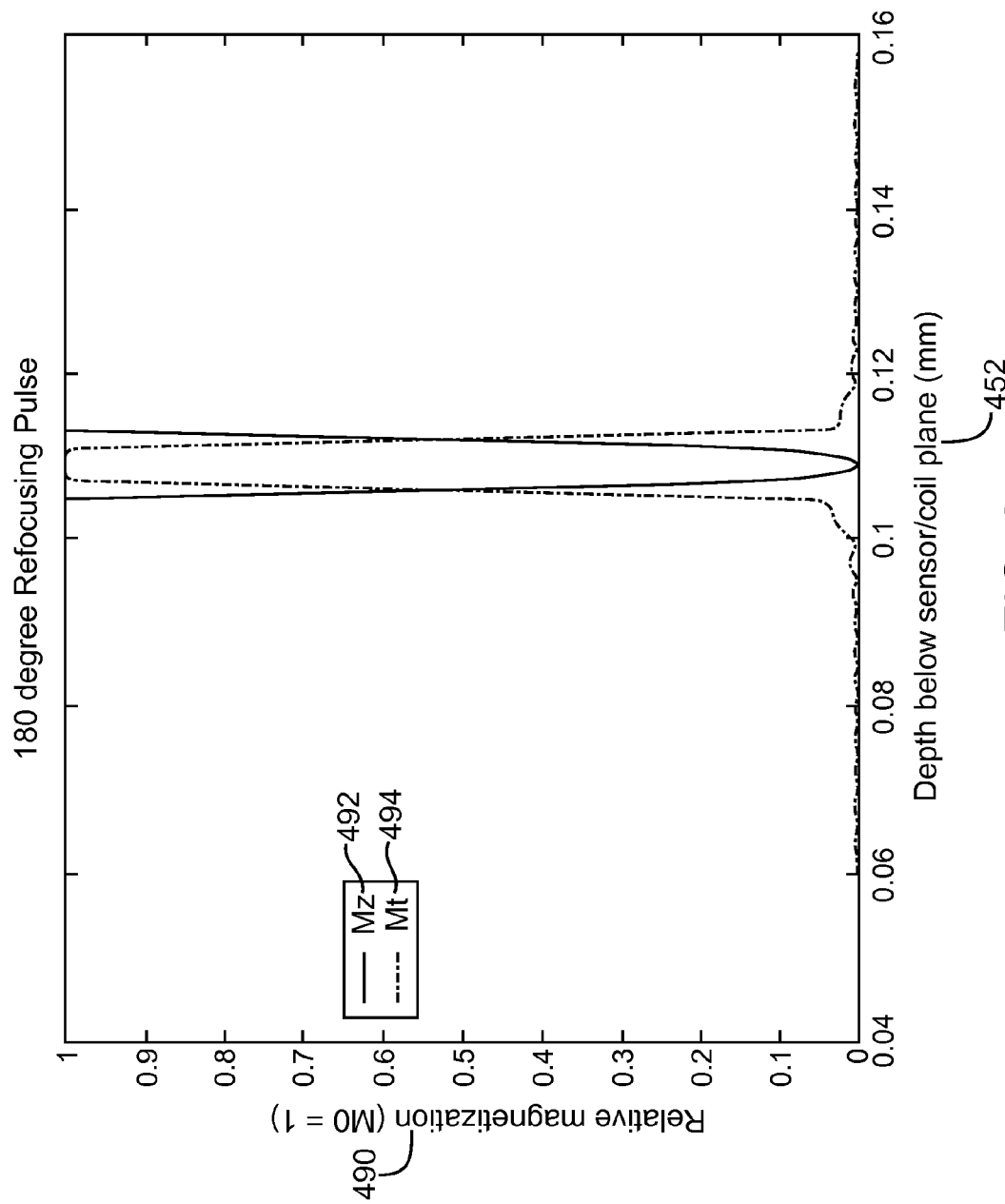
FIG. 8 shows a simulation of arterial wall proton magnetization following a 180° 'pancake' RF pulse applied to spins in the inhomogeneous static field of a small electromagnet.

FIG. 8. shows a simulation of arterial wall proton magnetization following a 180° 'pancake' RF pulse applied to spins in the inhomogeneous static field of a small electromagnet. More specifically, FIG. 8 shows the results of a simulation of the dynamics of the nuclear magnetization using the above pulse sequence and the static field profile (FIG. 7 and FIG. 6, respectively). The simulation shows relative magnetization 490 as a function of depth 452 for both longitudinal magnetization 492 (Mz) and transverse magnetization 494 (Mt). The simulation assumed 50 μs RF sinc pulses. Tissue T1 and T2 were 1 sec and 50 msec, respectively. A 10 μm thick slice was positioned 0.11 mm into the arterial wall by tuning the RF carrier frequency. Note the excellent slice profile achieved without applied field gradients, other than the intrinsic gradient of the electromagnet. These results show the ability to use the intrinsic gradient of the static field to discriminate MR signals at various depths below the coil. A Bloch simulation of the spins was conducted in Matlab using a library available from Brian Hargreaves at Stanford University (Hargreaves, B, Bloch Simulator. Downloaded from the World-Wide-Web: http://www-mrsrl.stanford.edu/~brian/mritools.html 2005.). The magnetization was assumed to be initially in the transverse plane, as it would be following a 90° pulse, just prior to application of the slice selective refocusing pulse. The slice profile was shown to be very good, and that embodiments do not require the use of gradient coils. The maximum RF amplitude can be as low as 13 gauss.

It may also be possible to use multiple broad band RF pulses to irradiate a thick slice and RF encode slice information. It is noted that although 180-deg refocusing pulses for producing spin echoes (SE) have been discussed, it is also possible to produce free induction decay signals (FID), the latter useful in the detection of short T2 components as well as for the imaging of susceptibility.

Information Display

The information obtained from the body lumen (a coronary artery in the embodiment under discussion) may provide spatially distributed information about the lesion that would not generally be viewable under fluoroscopy or other forms of imaging, such as CT, ultrasound or conventional MRI. The information can then displayed in a spatially correct orientation on a separately generated image of the body lumen, for example as described in U.S. Patent Publ. No. 2002/0115931 to Strauss, H. William; et al., published Aug. 22, 2002, entitled "Localizing intravascular lesions on anatomic images," the full disclosure of which is incorporated herein by reference.

The image of the body lumen can be externally or internally generated. Typically however, the anatomic image of the body lumen can be obtained with an external, image capture system such as angiography, fluoroscopy, CT or MRI. While angiography is one preferred embodiment because of its simplicity, cost effectiveness, speed, and superior frame rate resolution, it is equally possible to obtain the anatomic image of the body lumen using other imaging methods and systems. For example, other image capture systems include nuclear medicine imaging, computed tomography (CT), magnetic resonance imaging (MRI), ultrasound, electron beam computed tomography, or the like can be used.

In exemplary embodiments, the characterization of the lesion distribution is implemented in situ, i.e., within the body lumen being assessed, and can interrogate the body lumen over a relatively long distance to characterize the disseminated lesion in an efficient fashion. The methods and devices can provide real time, highly sensitive detection so that even minor differences between regions of plaque or other lesions can be determined.

For example, an intravascular catheter having detectors can be percutaneously introduced into the body lumen and advanced to the target region to acquire real time information and/or images of the lesion in the body lumen. A contrast medium can be released from the catheter to localize the position of the catheter during transit through the body lumen. The released contrast medium opacifies the body lumen and allows fluoroscopic images of the body lumen to be obtained. Unfortunately, the contrast medium delivered into the body lumen will diffuse over time and the image of the opacified body lumen can be lost. Consequently, the images of the body lumen can be saved in a computer memory to create "ghost images" of the body lumen that can later be recalled to create a background for the data obtained by the detectors. For a more complete discussion of "ghost" imaging of body lumens, see for example, Kaufman L, Kramer D M, and Hawryszko C., U.S. Pat. No. 5,155,435, and entitled "Method and Apparatus for Performing Interventional Medical Procedures Using MR Imaging of Interventional Device Superimposed with Ghost Patient Image", the full disclosure of which is incorporated herein by reference.

A coordinate system can be created for the body lumen to allow the data obtained by the catheter to be displayed with the anatomic image. To create the coordinate system for the body lumen, the user can track the position of markers or other fiducials on the catheter and fit a curve in the body lumen that accurately reflects the curvature of the body lumen. The systems of embodiments can use a tracing algorithm that is manual, computer-aided, or the like to create the coordinate system or a manual fitting program that allows the user to mark a few points (typically three or more) along the body lumen. The fitting program can fit straight lines or various order curves (second order curve, third order curve, forth order curve, or the like) between the points marked by the operator. The operator can manually interact with the final curve to fit the curve to the body lumen. If bi-plane angiography is used, this process can be repeated for both planes, so that the vessel coordinate system can be traced in a three-dimensional space.

Rigid and non rigid movements of the patient can affect the ability of the system to correctly superimpose the position of the catheter onto the stored anatomic image. Consequently, various methods can be used to correct for the rigid and non-rigid movement of the patient. For example, one method comprises placing a plurality of fixed fiducials or markers on the patient or patient platform to create a frame of reference for the anatomic images and the information acquired with the catheter. The anatomic images of the body lumen or images of the catheter may be rescaled, shifted, rotated, or the like so as to match the frames of reference of the images. To correct for non-rigid motion, the position of the plurality of fiducials can be tracked relative to each other. If the position of the fiducials become distorted during imaging, the computer can rescale the image to correct for the distortion of the acquired image so that the two images can be correctly registered.

Depending on the type of information that is desired, the catheters of embodiments can use detectors for measuring different characteristics about the lesion. Many embodiments of the catheters will include an array of position sensitive detectors that can transmit information related to azimuthal and longitudinal distribution of the lesion.

Once the detectors have obtained information about the lesion, the coordinate system has been defined, and the images have been registered, the saved anatomic image can be recalled and the information acquired by the catheter can be processed and displayed with the anatomic image. The information obtained with the detectors can be displayed in a variety of ways. For example, the resulting image of the body lumen can include a single image or multiple images that include histogram bars or graphs to indicate the longitudinal and azimuthal distribution of the detected information (e.g. MRI parameters), a color map indicating the distribution of the lesion, images having a varying brightness to indicate a distribution of the lesion, a three-dimensional view of the body lumen that can illustrate the distribution of the lesion, standard deviation marks in the form of bars or lines, cross-sections of the body lumen showing the azimuthal distribution of the lesion, or the like.

In one particular aspect, embodiments provide a method of localizing a lesion in a body lumen. The method comprises providing an image of the body lumen. Information is acquired about the lesion with a detecting device, and the information is displayed in a spatially correct distribution relative to the image of the body lumen.

In an exemplary configuration, the intravascular lesion detected is vulnerable plaque.

Embodiments provide a system for localizing lesions in a body lumen. The system includes a catheter body comprising at least one detector that can obtain information about the lesion. A plurality of markers are positioned on the distal portion of the catheter body that allow a user to track the azimuthal orientation of the distal portion of the catheter body. A computer is coupled to the detector. The computer is configured to superimpose the information obtained by the detector on an anatomic image of the body lumen.

While embodiments will find particular use in the diagnosis of lesions within blood vessels, additional embodiments will be useful in a wide variety of diagnostic and therapeutic procedures. The methodology of plaque detection can be extended to the detection of malignancies following the administration of a metabolic or specific MRI contrast agents. Examples of such applications include the differentiation of malignant from benign polyps during colonoscopy and of lung carcinoma from benign anatomy following lung screening by X-ray CT or by MRI.

Embodiments provide improved methods and apparatus for localizing and displaying lesions in body lumens, and in particular for displaying the distribution of vulnerable plaque in blood vessels. The methods can rely on acquiring a separate image of at least the target portion of the body lumen and superimposing information obtained about the lesion over the separately generated anatomic image. The information about the lesion can include, azimuthal distribution of the lesion, longitudinal distribution of the lesion in the body lumen, concentration or severity of the lesion, the type of lesion, biological activity occurring in the body lumen, temperature of the lesion, radiation counts, MRI parameters (signal, T1, T2, Hydrogen density, lipid content, water content, susceptibility, diffuision coefficient, and so on), x-ray density, paramagnetic, ferromagnetic or iodinated contrast agents, ultrasound signal, infrared or optical signature, and the like.

In exemplary embodiments, an external imaging method, such as fluoroscopy, angiography, x-ray imaging, nuclear medicine imaging, computed tomography (CT), magnetic resonance imaging (MRI), ultrasound, electron beam computed tomography, or the like are used to obtain an anatomic image of the body lumen.

In some exemplary embodiments, the vulnerable plaque lesion in the body lumen can first be marked to allow the catheter to better localize the position of the vulnerable plaque. For example, a labeled marker, such as a para- or ferromagnetic agent, can be introduced into the patient's blood vessel in such a way that the marker localizes within the lesion or target region which enables assessment of the type of plaque disposed within the blood vessel. Introduction of the labeled marker can be systemic (e.g., oral ingestion, injection or infusion to the patient's blood circulation, and the like), through local delivery (e.g. by catheter delivery directly to a target region within the blood vessel), or a combination of systemic and local delivery. After introduction of the marker to the patient, the marker can be taken up by the lesion at the target region and the amount of the marker, rate of uptake, distribution of the marker, or other marker characteristics can be analyzed to evaluate the distribution and severity of the lesion.

Figure 9:
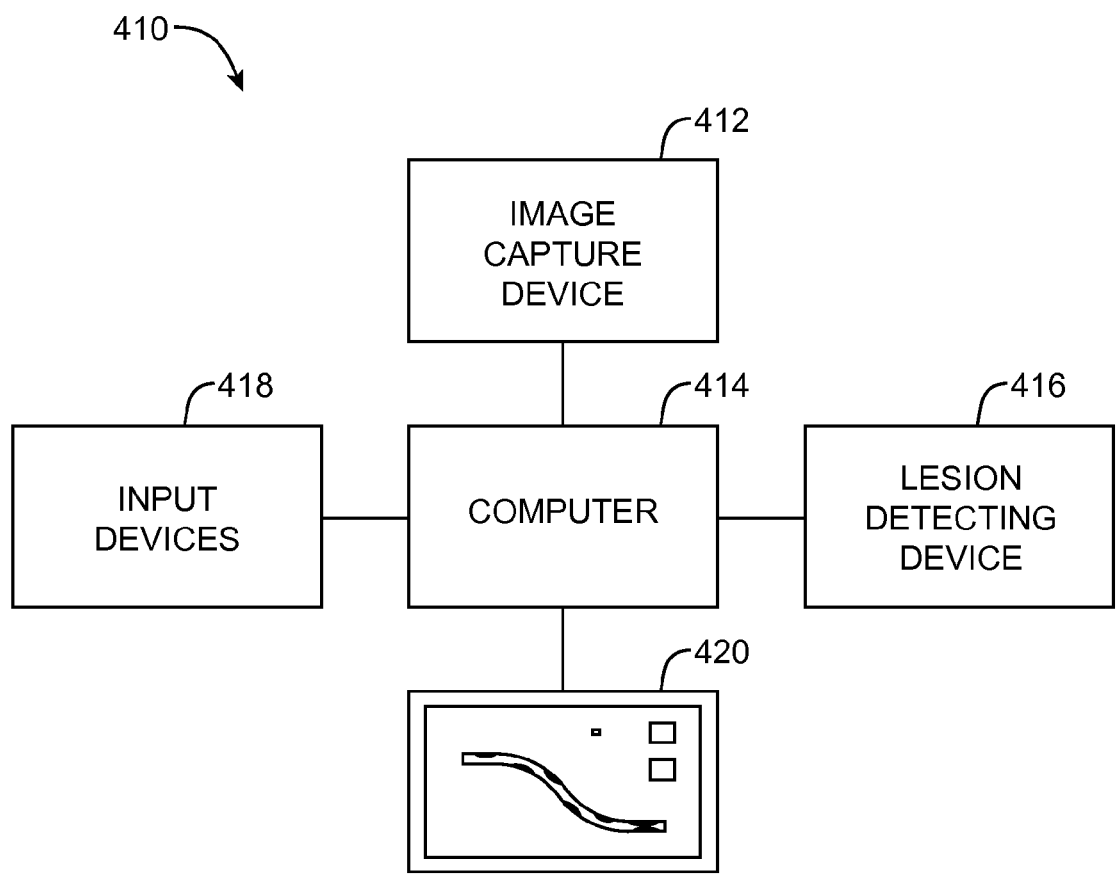
FIG. 9 illustrates an exemplary imaging system which can be combined with the sensor array.

FIG. 9 illustrates an exemplary imaging system 410 which can be combined with the sensor array as described above. The system 410 will typically include an image capture apparatus 412 that can capture an anatomic image of the body lumen. The image capture apparatus can include systems which generate angiographic images, CT images, MRI images, ultrasound images, nuclear medicine images, electron beam computed tomography images, or the like. The image capture apparatus 412 will typically be coupled to a computer 414 that has a processor and memory for processing and storing the anatomic image(s) of the body lumen. The computer may include input devices 418 such as a keyboard, a voice recognition system, a joystick, a mouse, buttons, foot pedals, or the like. A detecting device 416 such as an intravascular imaging catheter, as described above, can also be coupled to the computer 414 so as to feed data acquired with the catheter detectors into the computer 414. The computer 414 can be programmed to superimpose or otherwise display the information acquired by the catheter over (or adjacent) the anatomic image to display the information about the lesion in the body lumen on a display 420. In many embodiments the information will be placed over the body lumen in the correct anatomical position.

There are various ways of obtaining information. In one exemplary embodiment, the detector is positioned at a distal end of the target region and the detector is pulled proximally through the target region at a linearly constant speed. The speed of the catheter is tracked by the computer 14 so that the data obtained by the catheter detector(s) can be displayed in the correct anatomical position (both longitudinally and azimuthally) on the anatomic image of the body lumen. In another exemplary embodiment, a position sensitive catheter having a plurality of detectors is positioned at the target region and maintained in a stationary position.

In exemplary embodiments, the information obtained with the intravascular catheter 416 is displayed with the angiographic image. In some embodiments, the information is superimposed directly onto the anatomic image and is positioned in an anatomically correct position on the body lumen. In other embodiments, the information can be displayed as a separate image adjacent the anatomic image of the body lumen.

To compensate for the displacement of the images due to the patient's breathing the patient may be asked to hold his or her breath. Alternatively, a strain gage belt can be put around the patient's thorax to sense breathing motion, or a flow device can be placed over the patient's nose, and the data segregated into time periods for different parts of the respiratory cycle.

To compensate for rigid body motions (i.e. non distorting movements) radiopaque markers or fiducials (not shown) can be placed on the outside of the patient's body and/or the patient's platform to form a frame of reference. The computer 14 can be programmed to track the position of the markers on both the ghost image and the images acquired by the catheter so as to improve the accuracy of the superimposing of the image. Thus, if needed, the information obtained with the catheter 416 can be adjusted or shifted so that the image obtained with the image capture device 416 match the real time image of the body lumen.

To account for non-rigid motions (e.g. distortions or twisting of the patient's body) the number of fiducials on the patient's body can be increased so that at least two fiducials are along each axis. The computer will track the relative position and orientation of the plurality of fiducials in the real time image obtained by the catheter and will compare the measured distances to the distances of the fiducials in the ghost image. If the relative distances between the markers change, the computer will know that there has been a non-rigid movement in the body. Consequently, the images obtained with the catheter can be modified accordingly (e.g., scaled, enlarged, shrunk, rotated, or the like).

In addition to the embodiments described above, additional embodiments are possible. For example, the detectors can be used to detect a variety of properties and the information can be displayed to the operator in a variety of ways.

Moreover, instead of using a saved image with real time catheter images, a single image taken at a point when opacification has diminished enough to allow the fiducials to be viewed concurrently with the partially opacified vessel.

As another example, a contrast medium can be delivered into the body lumen to capture a location of the markers on the catheter. The catheter position data along with the data acquired with the detectors can be transferred to the computer 414 and the initial contrast angiogram image(s) can be combined by the computer 414 to superimpose the marker location on the coronary images.

While the exemplary embodiments have been described in some detail for clarity of understanding and by way of example, a variety of additional modifications, adaptations, and changes may be clear to those of skill in the art. Hence, the scope of the present invention is limited solely by the appended claims.

What is claimed is:

1. A device for NMR mapping of a material, the device comprising:
   a magnet to orient nuclei of the material;
   a coil to excite the oriented nuclei and induce an emission of NMR signals; and
   an array of magnetoresistive sensors to detect at least one of a magnetic field amplitude or a magnetic field phase of said NMR signals, wherein the magnetoresistive sensors are arranged to detect the NMR signals in quadrature, each sensor occupying an array site to map detected signal locations.

2. The device of claim 1 wherein each sensor is sensitive to a magnetic field along a single direction in a sensor plane, the axes of the sensors arranged to detect the NMR signals in quadrature.

3. The device of claim 1 wherein the magnetoresistive sensors comprise at least one of an anisotropic magnetoresistive sensor, a tunneling magnetoresistive sensor or a colossal magnetoresistive sensor.

4. The device of claim 1 wherein the magnetoresistive sensors comprise at least one giant magnetoresistive sensor.

5. The device of claim 1 wherein the magnet is positioned in proximity to the sensor array.

6. The device of claim 1 wherein the magnet comprises at least one of an electromagnet or a permanent magnet.

7. The device of claim 1 wherein the radiofrequency coil is positioned in proximity to the sensor array.

8. The device of claim 7 wherein the magnet is positioned in proximity to the coil and the sensor array.

9. The device of claim 7 wherein the material comprises tissue of a patient, the processor to superimpose the image on an anatomic image of the patient.

10. The device of claim 9 wherein the image comprises at least one of a radiographic projection image, a CT image, an MRI image, or an ultrasound image.

11. The device of claim 1 further comprising:
    a display to show an NMR image of the material to a user; and
    a processor to map the signals from the sensors to the image.

12. The device of claim 1 wherein the NMR signals comprise at least one of a free induction decay signal, a spin echo signal or a sequence of spin echo signals.

13. The device of claim 1 wherein the NMR signals comprise encoding to determine a slice for the locations of the signals in the material.

14. The device of claim 13 wherein the magnet generates a static inhomogeneous magnetic field and the signal encoding comprising at least one of a radiofrequency excitation phase encoding, a radiofrequency excitation frequency encoding, or a radiofrequency excitation amplitude encoding in the static inhomogeneous magnetic field.

15. The device of claim 1 wherein the NMR signal correlates with at least one of a nuclear density, a spin lattice relaxation time, a transverse relaxation time, a diffusion, a magnetization transfer, a flow or a spectral distribution within the material.

16. The device of claim 1 further comprising at least one contrast agent to enhance the NMR signals.

17. The device of claim 1 further comprising a protective enclosure to protect at least one of the sensors, the coil or the magnet.

18. The device of claim 1 further comprising a structure having a cavity formed therein to position the material in the cavity near the sensors.

19. A device for NMR mapping of a material, the device comprising:
   several magnets to orient nuclei of the material;
   a coil to excite the oriented nuclei and induce an emission of NMR signals; and
   an array of magnetoresistive sensors to detect at least one of a magnetic field amplitude or a magnetic field phase of said NMR signals, each sensor occupying an array site to map detected signal locations, wherein each of the several magnets is positioned in proximity to at least one sensor.

20. A device for NMR mapping of a material, the device comprising:
   a magnet to orient nuclei of the material;
   a coil to excite the oriented nuclei and induce an emission of NMR signals;
   an array of magnetoresistive sensors to detect at least one of a magnetic field amplitude or a magnetic field phase of said NMR signals, each sensor occupying an array site to map detected signal locations, wherein the radiofrequency coil is positioned in proximity to the sensor array; and
   an external induction coil to power the radiofrequency coil with inductive coupling.

21. A device for NMR mapping of a material, the device comprising:
   a magnet to orient nuclei of the material;
   a coil to excite the oriented nuclei and induce an emission of NMR signals;
   an array of magnetoresistive sensors to detect at least one of a magnetic field amplitude or a magnetic field phase of said NMR signals, each sensor occupying an array site to map detected signal locations, wherein the radiofrequency coil is positioned in proximity to the sensor array; and
   a conductor to conductively couple the radiofrequency coil to a power source.

\* \* \* \* \*